United States Patent
Park et al.

(10) Patent No.: US 10,280,178 B2
(45) Date of Patent: May 7, 2019

(54) COMPOUND FOR INHIBITING BINDING BETWEEN DX2 PROTEIN AND P14/ARF PROTEIN, AND PHARMACEUTICAL COMPOSITION FOR TREATING OR PREVENTING CANCER DISEASE CONTAINING SAME AS EFFECTIVE INGREDIENT

(71) Applicants: PUSAN NATIONAL UNIVERSITY INDUSTRY-UNIVERSITY COOPERATION FOUNDATION, Busan (KR); THE INDUSTRY & ACADEMIC COOPERATION IN CHUNGNAM NATIONAL UNIVERSITY (IAC), Daejeon (KR)

(72) Inventors: Bum Joon Park, Busan (KR); Gyu Yong Song, Daejeon (KR); Ah-Young Oh, Busan (KR); Jee-Hyun Lee, Daejeon (KR); Jin-Hyuk Her, Daejeon (KR)

(73) Assignees: PUSAN NATIONAL UNIVERSITY INDUSTRY-UNIVERSITY COOPERATION FOUNDATION, Busan (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 0 days.

(21) Appl. No.: 16/100,226

(22) Filed: Aug. 10, 2018

(65) Prior Publication Data

US 2018/0362540 A1    Dec. 20, 2018

Related U.S. Application Data

(62) Division of application No. 15/323,099, filed as application No. PCT/KR2015/006701 on Jun. 30, 2015, now Pat. No. 10,072,021.

(30) Foreign Application Priority Data

Jun. 30, 2014 (KR) ........................ 10-2014-0081396
Jun. 29, 2015 (KR) ........................ 10-2015-0092057

(51) Int. Cl.
C07D 493/04    (2006.01)
A61K 31/366    (2006.01)
G01N 33/574    (2006.01)
A61K 31/352    (2006.01)
A61K 45/06     (2006.01)
C12Q 1/68      (2018.01)
A61K 31/35     (2006.01)
A61K 31/34     (2006.01)

(52) U.S. Cl.
CPC ............ *C07D 493/04* (2013.01); *A61K 31/34* (2013.01); *A61K 31/35* (2013.01); *A61K 31/352* (2013.01); *A61K 31/366* (2013.01); *A61K 45/06* (2013.01); *C12Q 1/68* (2013.01); *G01N 33/574* (2013.01); *G01N 33/57423* (2013.01)

(58) Field of Classification Search
CPC .... A61K 45/06; A61K 31/366; C07D 493/04; G01N 33/57423
USPC ........................................................ 424/649
See application file for complete search history.

(56) References Cited

PUBLICATIONS

Lee et al. European Journal of Medicinal Chemistry (2010),45(12), 5567-5575.*
Dongsool Yim, et al., "A Novel Anticancer Agent, Decursin, Induces G1 Arrest and Apoptosis in Human Prostate Carcinoma Cells", Research Article, Feb. 1, 2005, pp. 1035-1044, vol. 65(3).
Ah-Young Oh, "AIMP2 alternative splicing variant, DX2 produces multi-type lung cancers by inhibition of p14/ARF-pRb pathway", Department of Biological Sciences Graduate school of Pusan National University, Feb. 2013, pp. 1-67.
Hyo Jeong Lee, "In vivo Anti-Cancer Activity of Korean Angelica Gigas and its Major Pyranocoumarin Decursin", The American Journal of Chinese Medicine, 2009, pp. 127-142, vol. 37, No. 1.
Kyeong Lee, "Synthesis of (S)-(þ)-decursin and its analogues as potent inhibitors of melanin formation in B16 murine melanoma cells", European Journal of Medicinal Chemistry, 2010, pp. 5567-5575, vol. 45.

* cited by examiner

*Primary Examiner* — Kahsay Habte
(74) *Attorney, Agent, or Firm* — Revolution IP, PLLC

(57) ABSTRACT

Disclosed is a new compound that inhibits binding between a DX2 protein and a p14/ARF protein, a pharmaceutical composition including the new compound as an effective component for treating or preventing a cancer disease, an anticancer adjuvant for improving an anticancer effect of a drug-resistant anticancer drug, and a composition including an AIMP2-DX2 protein or a fragment thereof for diagnosing lung cancer.

5 Claims, 16 Drawing Sheets

Specification includes a Sequence Listing.

```
SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: AIMP2-DX2 forward primer

<400> SEQUENCE: 1
aacgtgcacg gcaggagcta c                                          21

<210> SEQ ID NO 2
<211> LENGTH: 21
<212> TYPE: DNA
<213> ORGANISM: Artificial Sequence
<220> FEATURE:
<223> OTHER INFORMATION: AIMP2-DX2 reverse primer

<400> SEQUENCE: 2
ccagctgata gtcttggcgg g                                          21

<210> SEQ ID NO 3
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 3
atcttccagg agcgagatcc c                                          21

<210> SEQ ID NO 4
<211> LENGTH: 21
<212> TYPE: DNA
<213> ORGANISM: Artificial Sequence
<220> FEATURE:
<223> OTHER INFORMATION: GAPDH reverse primer

<400> SEQUENCE: 4
agtgagcttc ccgttcagct c                                          21

<210> SEQ ID NO 5
<211> LENGTH: 251
<212> TYPE: PRT
```

<213> ORGANISM: Artificial Sequence
<220> FEATURE:
<223> OTHER INFORMATION: AIMP2-DX2 of Homo sapiens

<400> SEQUENCE: 5

```
Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Asp Tyr Gly
        35                  40                  45

Ala Leu Lys Asp Ile Val Ile Asn Ala Asn Pro Ala Ser Pro Pro Leu
    50                  55                  60

Ser Leu Leu Val Leu His Arg Leu Leu Cys Glu His Phe Arg Val Leu
65                  70                  75                  80

Ser Thr Val His Thr His Ser Ser Val Lys Ser Val Pro Glu Asn Leu
                85                  90                  95

Leu Lys Cys Phe Gly Glu Gln Asn Lys Lys Gln Pro Arg Gln Asp Tyr
            100                 105                 110

Gln Leu Gly Phe Thr Leu Ile Trp Lys Asn Val Pro Lys Thr Gln Met
        115                 120                 125

Lys Phe Ser Ile Gln Thr Met Cys Pro Ile Glu Gly Glu Gly Asn Ile
    130                 135                 140

Ala Arg Phe Leu Phe Ser Leu Phe Gly Gln Lys His Asn Ala Val Asn
145                 150                 155                 160

Ala Thr Leu Ile Asp Ser Trp Val Asp Ile Ala Ile Phe Gln Leu Lys
                165                 170                 175

Glu Gly Ser Ser Lys Glu Lys Ala Ala Val Phe Arg Ser Met Asn Ser
            180                 185                 190

Ala Leu Gly Lys Ser Pro Trp Leu Ala Gly Asn Glu Leu Thr Val Ala
        195                 200                 205

Asp Val Val Leu Trp Ser Val Leu Gln Gln Ile Gly Gly Cys Ser Val
    210                 215                 220

Thr Val Pro Ala Asn Val Gln Arg Trp Met Arg Ser Cys Glu Asn Leu
225                 230                 235                 240

Ala Pro Phe Asn Thr Ala Leu Lys Leu Leu Lys
                245                 250
```

<210> SEQ ID NO 6
<211> LENGTH: 243
<212> TYPE: PRT
<213> ORGANISM: Artificial Sequence
<220> FEATURE:
<223> OTHER INFORMATION: AIMP2-DX2 of Homo sapiens

<400> SEQUENCE: 6

```
Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Asp Tyr Gly
        35                  40                  45

Ala Leu Lys Asp Ile Val Ile Asn Ala Asn Pro Ala Ser Pro Pro Leu
    50                  55                  60

Ser Leu Leu Val Leu His Arg Leu Leu Cys Glu His Phe Arg Val Leu
65                  70                  75                  80
```

-continued

```
Ser Thr Val His Thr His Ser Ser Val Lys Ser Val Pro Glu Asn Leu
            85              90              95

Leu Lys Cys Phe Gly Glu Gln Asn Lys Lys Gln Pro Arg Gln Asp Tyr
            100             105             110

Gln Leu Gly Phe Thr Leu Ile Trp Lys Asn Val Pro Lys Thr Gln Met
            115             120             125

Lys Phe Ser Ile Gln Thr Met Cys Pro Ile Glu Gly Glu Gly Asn Ile
            130             135             140

Ala Arg Phe Leu Phe Ser Leu Phe Gly Gln Lys His Asn Ala Val Asn
145             150             155             160

Ala Thr Leu Ile Asp Ser Trp Val Asp Ile Ala Ile Phe Gln Leu Lys
            165             170             175

Glu Gly Ser Ser Lys Glu Lys Ala Ala Val Phe Arg Ser Met Asn Ser
            180             185             190

Ala Leu Gly Lys Ser Pro Trp Leu Ala Gly Asn Glu Leu Thr Val Ala
            195             200             205

Asp Val Val Leu Trp Ser Val Leu Gln Gln Ile Gly Gly Cys Ser Val
            210             215             220

Thr Val Pro Ala Asn Val Gln Arg Trp Met Arg Ser Cys Glu Asn Leu
225             230             235             240

Ala Pro Phe
```

COMPOUND FOR INHIBITING BINDING BETWEEN DX2 PROTEIN AND P14/ARF PROTEIN, AND PHARMACEUTICAL COMPOSITION FOR TREATING OR PREVENTING CANCER DISEASE CONTAINING SAME AS EFFECTIVE INGREDIENT

CROSS REFERENCE TO PRIOR APPLICATION

This application is a divisional Application of U.S. patent application Ser. No. 15/323,099 filed on Dec. 30, 2016 under 35 U.S.C. § 120, which is the 35 U.S.C. § 371 national stage of International application PCT/KR2015/006701 filed on Jun. 30, 2015, which claims priority to Korean applications 10-2015-0092057 filed on Jun. 29, 2015 and 10-2014-0081396 filed on Jun. 30, 2014, respectively.

BACKGROUND

The present invention relates to a new compound that inhibits binding between a DX2 protein and a p14/ARF protein, a pharmaceutical composition including the new compound as an effective component for treating or preventing a cancer disease, an anticancer adjuvant for improving an anticancer effect of a drug-resistant anticancer drug, and a composition including an AIMP2-DX2 protein or a fragment thereof for diagnosing lung cancer.

Lung cancer is mainly caused by carcinogens, and incidence of lung cancer has been on a rising trend worldwide. In South Korea, lung cancer having the highest mortality rate among all cancers is regarded as one of the most serious diseases. Lung cancer is divided into two groups, small cell lung cancer (SCLC) and non small cell lung cancer (NSCLC), and the NSCLC is also divided into sub-groups: adenocarcinoma, squamous carcinoma, large cell carcinoma, and adenosquamous carcinoma, depending on lung tissue types. Clinical manifestations, such as areas prone to occur depending on different lung tissue types, progression type and speed, and symptoms, may vary as well as treatment methods.

Most of lung cancers cannot be treated by chemotherapy and radiation therapy. Chemotherapy and radiation therapy may be used by reducing a size of SCLC while complete treatment cannot be expected from chemotherapy and radiation therapy. Since an anticancer drug is less effective in NSCLC than SCLC, the treatment of lung cancer using chemotherapy only is almost impossible. Instead, complete removal of tumors in a surgical manner is the only effective treatment. However, about 30% or less of patients with lung cancer have tumors that cannot be totally resected when being diagnosed. In addition, only one-third or less of the patients survive for 5 years after surgical resection is done.

Therefore, there is a great demand for a method of more accurately detecting the early diagnosis of lung cancer and the spread of cancer and more effectively treating lung cancer.

SUMMARY

An object of the present invention is to provide a new compound that inhibits binding between a DX2 protein and a p14/ARF protein in consideration of development of a new useful compound for treatment of a cancer disease including lung cancer.

In addition, another object of the present invention is to provide a pharmaceutical composition for treating or preventing a cancer disease, the pharmaceutical composition including, as an effective compound, a compound that inhibits binding between a DX2 protein and a p14/ARF protein.

In addition, another object of the present invention is to provide an anticancer adjuvant for improving an anticancer effect of a drug-resistant anticancer drug, the anticancer adjuvant including, as an effective component, a compound that inhibits binding between a DX2 protein and a p14/ARF protein.

In addition, another object of the present invention is to provide a composition for diagnosing lung cancer, the composition including an AIMP2-DX2 protein or a fragment thereof.

To achieve the objectives above, the present invention provides a compound represented by Formula 1 or 2:

[Formula 1]

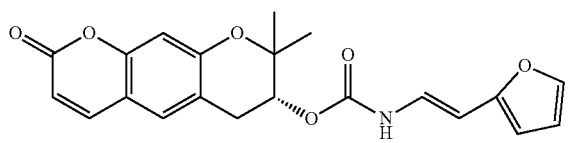

[Formula 2]

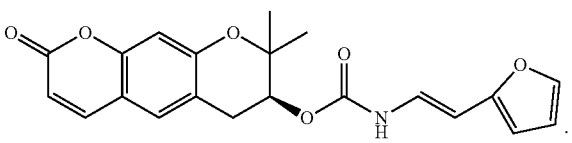

In addition, the present invention provides a pharmaceutical composition for treating or preventing a cancer disease, the pharmaceutical composition including, as an effective component, a compound represented by Formula 1, 2, or 3:

[Formula 1]

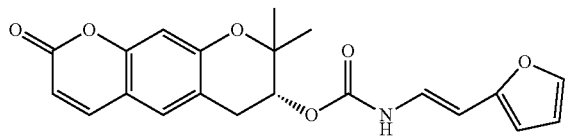

[Formula 2]

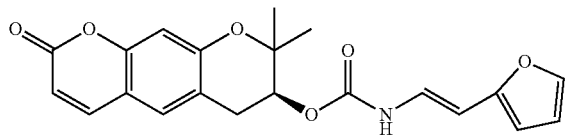

[Formula 3]

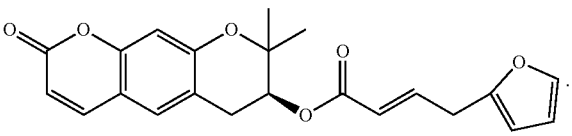

In addition, the present invention provides a pharmaceutical composition for inhibiting drug resistance of an anticancer drug, the pharmaceutical composition including, as an effective component, a compound represented by Formula 1, 2, or 3.

In addition, the present invention provides a pharmaceutical composition for treating or preventing a cancer disease, the pharmaceutical composition including, as effective components, a compound represented by Formula 1, 2, or 3 and an anticancer drug.

In addition, the present invention provides a composition for diagnosing lung cancer, the composition including an AIMP2-DX2 protein or a fragment thereof.

In addition, the present invention provides a method of detecting an autoantibody to an AIMP2-DX2 protein to provide information for lung cancer diagnosis, the method including: (a) detecting an antibody to an AIMP2-DX2 protein from a sample derived from a subject; and (b) determining that a subject has lung cancer or is susceptible to lung cancer if an amount of the detected antibody in the subject increases as compared with a normal person.

In addition, the present invention provides a kit for diagnosing lung cancer, the kit including an AIMP2-DX2 protein or a fragment thereof.

According to the present invention, a compound that inhibits interaction of a DX2 protein with a p14/ARF protein may be selected. An analogous compound to the selected compound is synthesized, and a review of in vitro and in vivo anticancer effects of the analogous compound shows that the compound has an excellent anticancer effect. In particular, in a cell line which is resistant to an anticancer drug such as Adriamycin, it is confirmed that the a compound that inhibits interaction between a DX2 protein and a p14/ARF protein is treated so that resistance of an anticancer drug against Adriamycin is inhibited while an anticancer effect of the anticancer drug is improved. Accordingly, the disclosed compound that inhibits interaction between a DX2 protein and a p14/ARF protein can be significantly used as an anticancer drug or anticancer adjuvant for a cancer disease such as lung cancer.

In addition, the present invention provides a composition and a kit, each of which includes an AIMP2-DX2 protein or a fragment thereof for diagnosing lung cancer. The composition and the kit may be used to identify incidence of lung cancer only by using a serum sample of a subject.

BRIEF DESCRIPTION OF THE DRAWINGS

FIG. 6 shows results of soft agar colony formation assay obtained after H128 cells which are SCLC cell lines were treated with SLCB050 treatment on;

DETAILED DESCRIPTION

Hereinafter, the present invention will be described in detail. Korean Patent Application No. 2014-0113543 discloses that DX2 inhibits induction of carcinogen-inducible p14/ARF so that a specific binding inhibitor of DX2 and p14/ARF can be used as an anticancer drug. In this regard, the present invention is completed by discovering a specific binding inhibitor of DX2 and p14/ARF and confirming an anticancer effect of the inhibitor.

The present invention provides a compound represented by Formula 1 or 2:

[Formula 1]

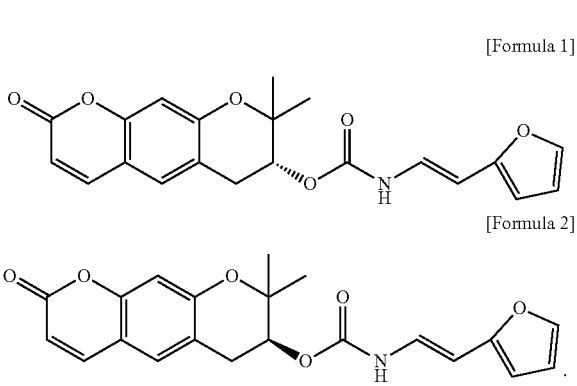

[Formula 2]

Here, the compound represented by Formula 1 is named as HJH141204, and the compound represented by Formula 2 is named as HJH141206. These compounds may inhibit binding between a DX2 protein and a p14/ARF.

In addition, a compound represented by Formula 3 is named as SLCB050.

[Formula 3]

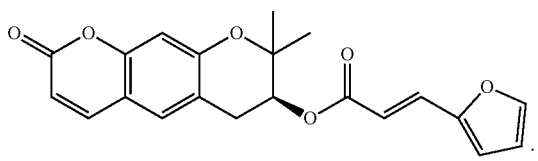

Figure 1:
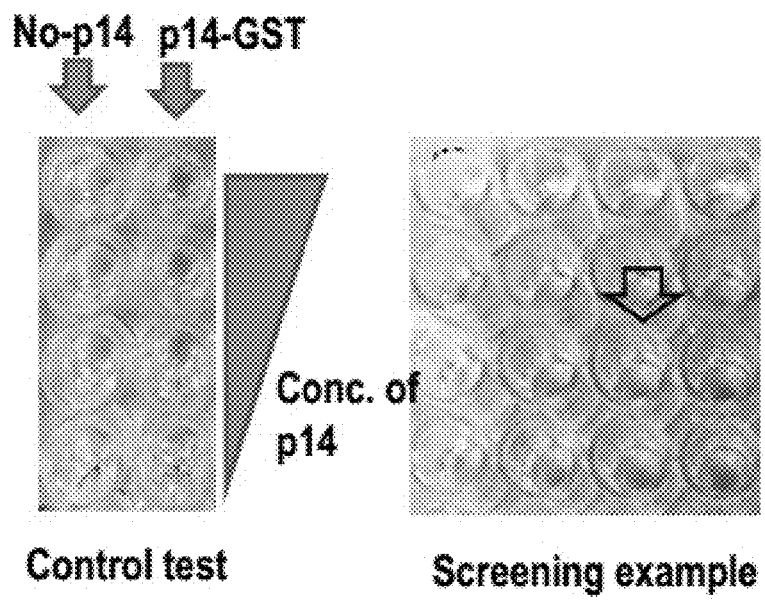
FIG. 1 shows an ELISA-based screening method for screening a specific inhibitor of DX2 and p14/ARF binding.

In detail, referring to drawings, the compound according to an embodiment of the present invention which is a specific binding inhibitor of DX2 and p14/ARF was screened by using an ELISA-based screening method of FIG. 1. Based on the screening reaction system, increases in ELISA values with increasing concentrations of p14/ARF were measured. However, in the case the treatment of a specific binding inhibitor of DX2 and p14/ARF, such as SLCB050, ELISA reaction was considerably reduced. Thus, by using the ELISA-based screening method, compounds that are specific binding inhibitors of DX2 and p14/ARF were primarily screened.

Figure 2:
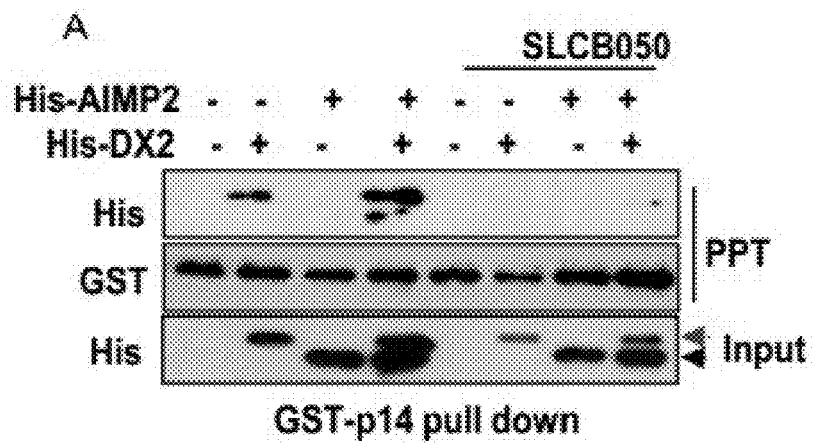
FIG. 2 illustrates A showing results of GST pull-down assay, B showing results of immunoprecipitation analysis, and C showing results obtained by performing protein binding analysis using a His-DX2 protein as an inhibitory effect of SLCB050 on DX2-p14/ARF binding (IP: a group binding to a protein for precipitation, Sup: a group not binding to a protein from which supernatant of the precipitate is separated, Input: cell debris)
Figure 2:
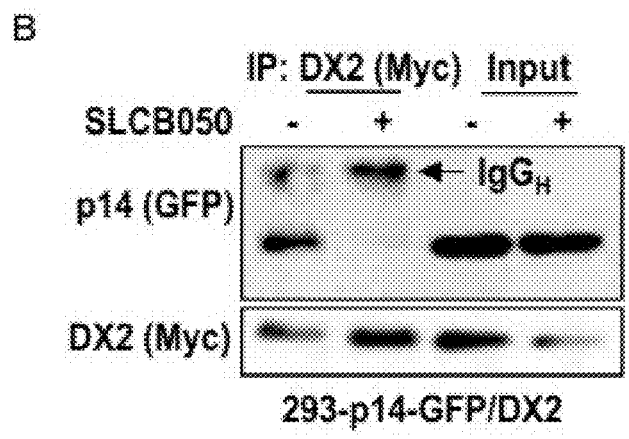
Figure 2:
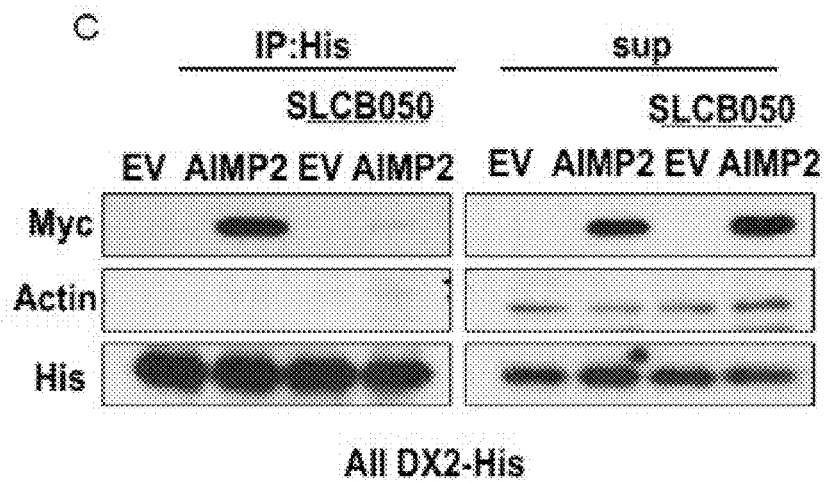
Figure 3:
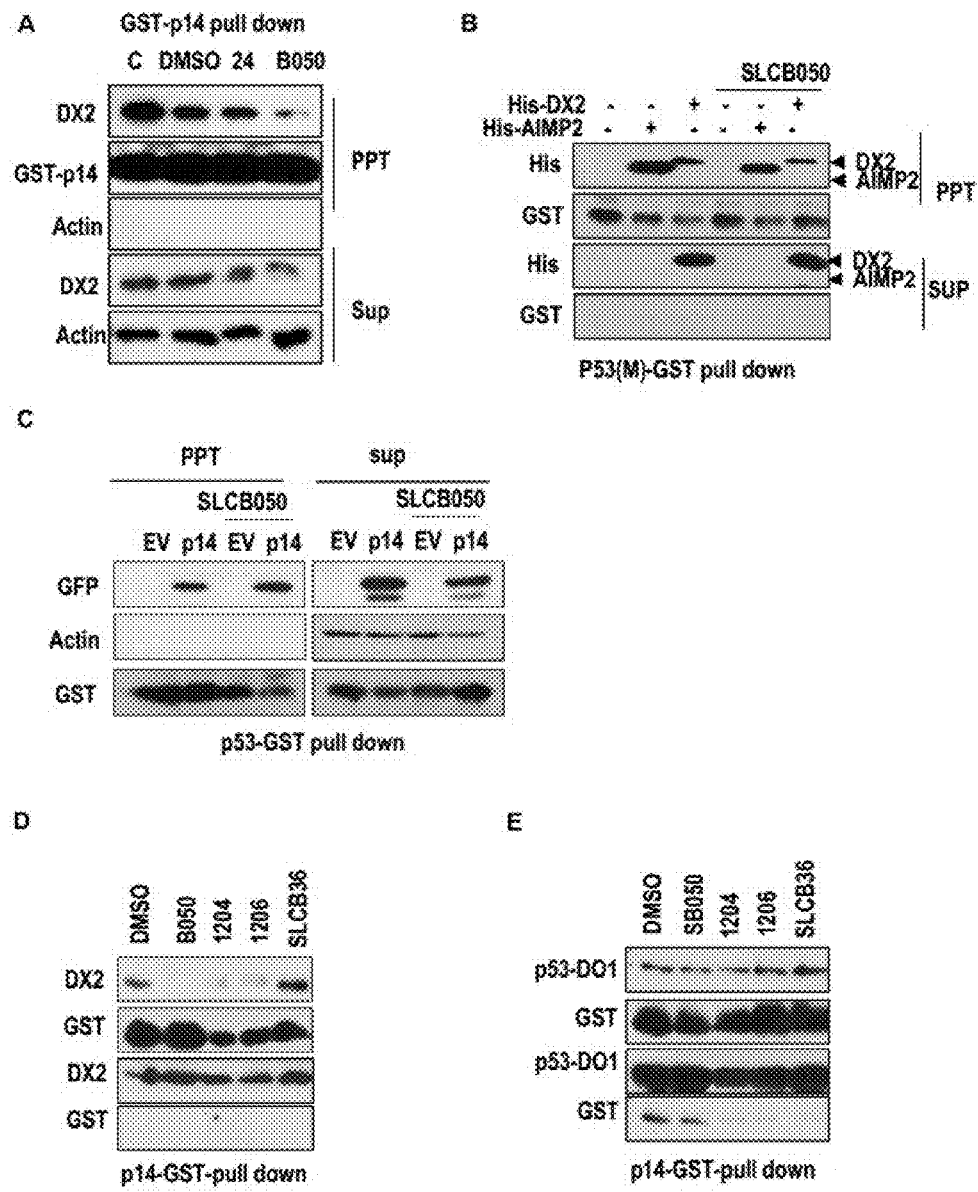
FIG. 3 illustrates A, B, C showing results of GST pull-down assay to confirm interaction of SLCB050 with a DX2-specific region, and D, E showing results of GST pull-down assay to confirm inhibitory effects of HJH141204, HJH141206, and SLCB36 on DX2-p14/ARF binding (PPT: a group binding to a protein for precipitation, Sup: a group not binding to a protein from which supernatant of the precipitate is separated)

FIG. 2A confirms that SLCB050 completely blocked the DX2-p14/ARF binding through GST pull-down assay. FIG. 2B confirms that SLCB050 inhibited the interaction of p14/ARF with DX2 in cells through immunoprecipitation analysis. Here, contransfected 293 cells were allowed to react with MG132 before immunoprecipitation analysis to prevent reduction of two proteins, and after performing SLCB050 treatment (10 μM, 6 hours), immunoprecipitation assay was performed on the cells by using Myc antibodies (DX2). FIG. 2C shows that binding between DX2 and AIMP2 was reduced by SLCB050 treatment in protein binding assay using His-DX2 protein, in terms of inhibitory effect of SLCB050 on the binding between DX2 and AIMP2. In addition, since SLCB050 selectively inhibited DX2-p14/ARF binding as shown in FIG. 3A, but not on p53-AIMP2 or DX2 binding as shown in FIG. 3B and p14/ARF binding as shown in FIG. 3C, it was confirmed that SLCB050 would be interacted with DX2-specific region.

In addition, HJH141204, HJH141206, and SLCB36, which are compounds similar to SLCB050, were each synthesized, and the GST pull-down assay was performed thereon to verify inhibitory effect on DX2-p14/ARF binding. As a result, as shown in FIGS. 3D and 3E, SLCB050, HJH141204, and HJH141206 showed inhibitory effects on DX2-p14/ARF binding and did not affect the interaction of p53-p14/ARF, whereas SLCB36 did not show inhibitory effect on both binding. Accordingly, it was confirmed that inclusion of a ribose ring structure in the compounds is required for the binding inhibition.

Figure 4:
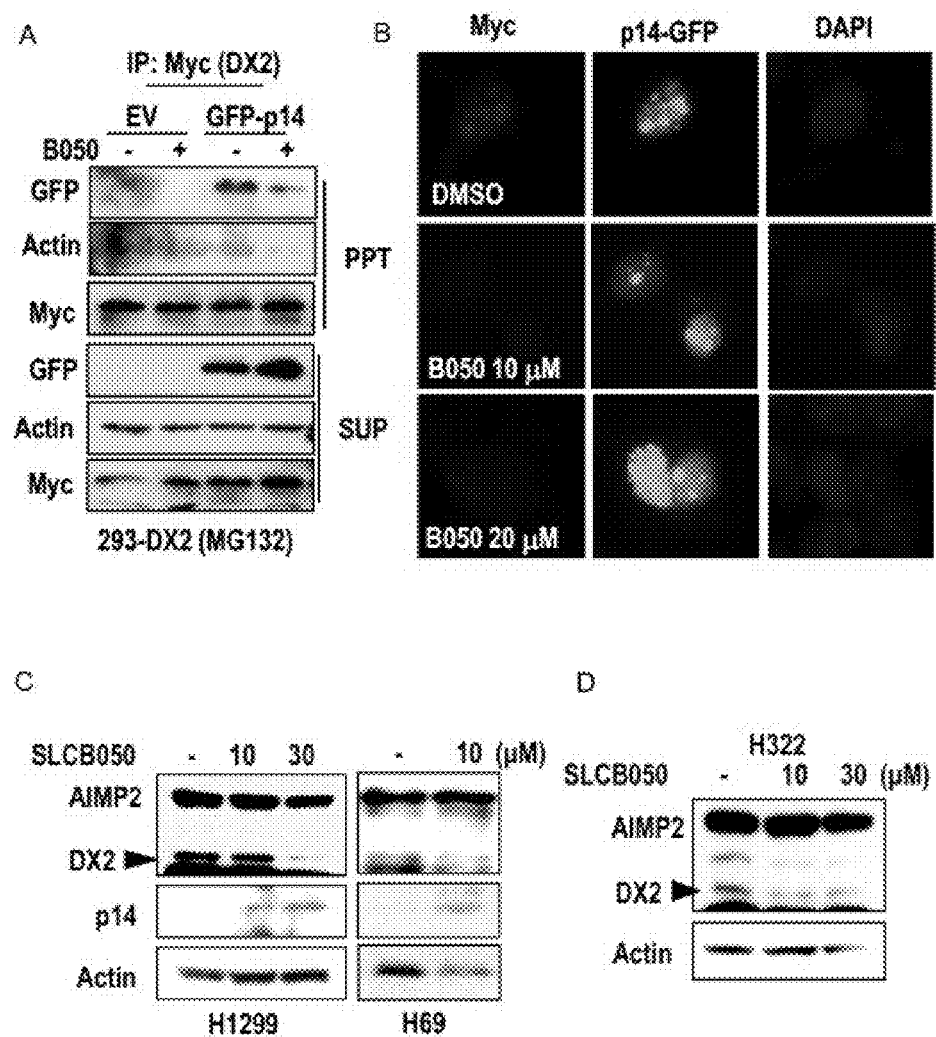
FIG. 4 illustrates A showing dissociation of DX2 and p14/ARF after performing SLCB050 treatment, B showing differences in localization of DX2 and p14/ARF after SLCB050 treatment, C showing SLCB050 treatment effects on NSCLC cell line H1299 and SCLC cell line H69, and D showing SLCB050 treatment effects on p14/ARF-deficient H322 cells.

FIG. 4A shows results obtained by detection of dissociation of DX2 and p14/ARF through immunoprecipitation analysis. Here, 293 cells were transfected with indicating vectors for 24 hours and was allowed to react with MG132 and SLCB050 for 6 hours. FIG. 4B shows differences in localization of DX2 and p14/ARF after the proteins were treated with SLCB050. Here, the interaction of DX2 with p14/ARF was blocked by SLCB050 treatment (10μM, 6 hours) so that DX2 was decreased and p14/ARF was increased in the nucleoplasm. In addition, FIG. 4C shows SLCB050 treatment effects on NSCLC cell line H1299 and SCLC cell line H69, and more particularly, shows that SLCB050 treatment decreases DX2, but increases p14/ARF in NSCLC cell line H1299 and SCLC cell line H69. In addition, FIG. 4D shows SLCB050 treatment effects on p14/ARF-deficient H322 cells. Here, DX2 levels decreased considerably in the p14/ARF-deficient H322 cells in response to SLCB050 treatment.

Figure 5:
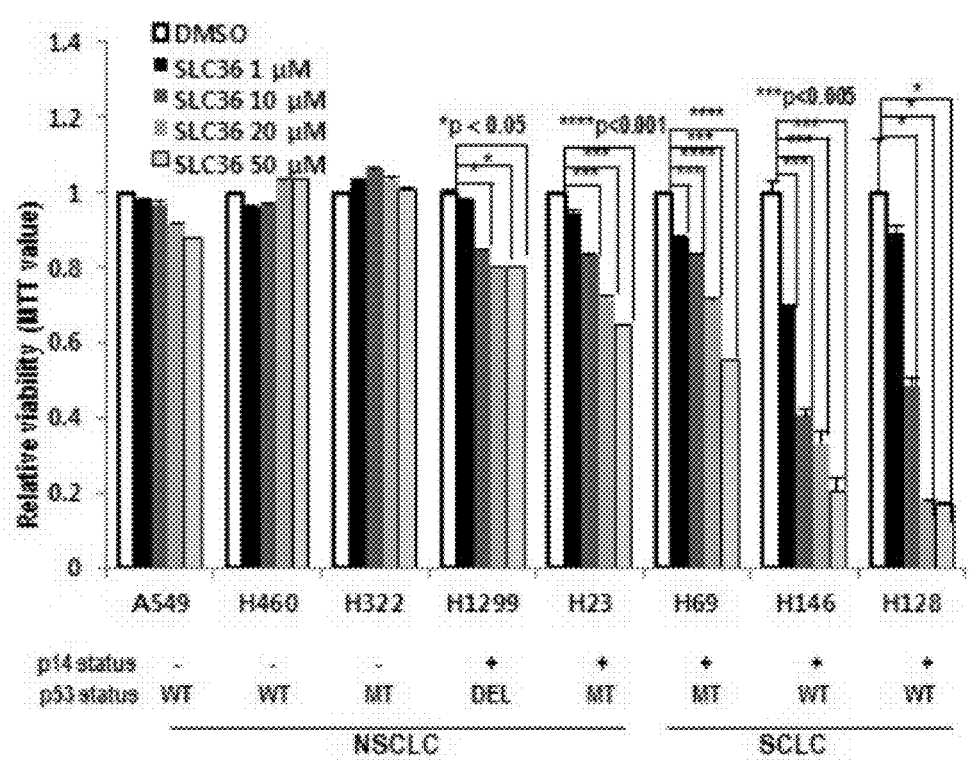
FIG. 5 shows viability of various human lung cancer cell lines obtained after performing SLCB050 treatment thereon.

FIG. 5 shows viability of various human lung cancer cell lines after the cell lines were treated with SLCB050 for 24 hours, wherein the viability was determined by MTT assay. Here, SCLC cells were very sensitive to SLCB050.

Figure 6:
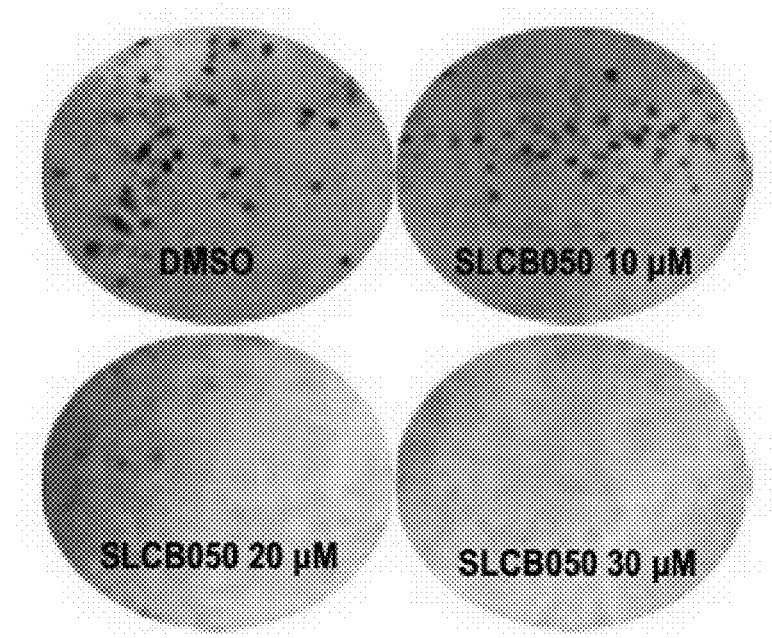
Figure 6:
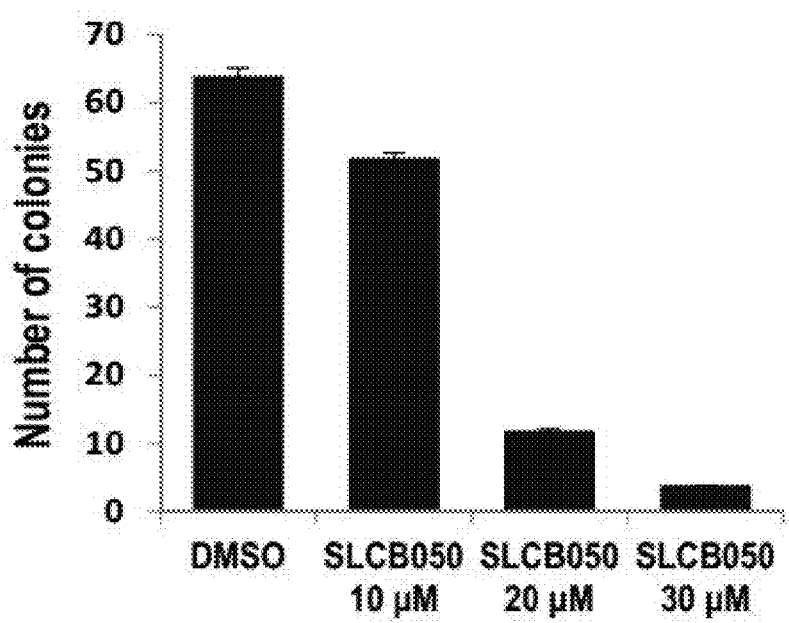

FIG. 6 shows results of soft agar colony formation assay. H128 cells which are SCLC cell lines were seeded in soft agar plates and allowed to react with SLCB050 for 48 hours, and then, the cells were examined after staining the cells with trypan blue. SLCB050 reduced the number of colonies in a dose-dependent manner.

Figure 7:
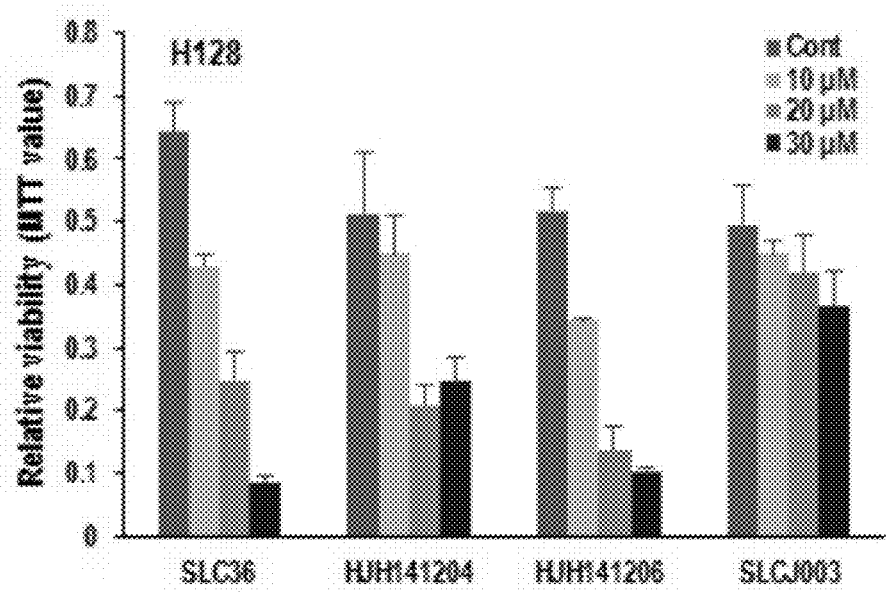
FIG. 7 shows viability of H128 cells which are SCLC cell lines after the cells were treated with SLCB050, HJH141204, HJH141206, and SLCB36.

FIG. 7 shows viability of H128 cells which are SCLC cell lines after the cells were treated with SLCB050, HJH141204, HJH141206, and SLCB36. The SLCB050, HJH141204, and HJH141206 treatments reduced the viability of H128 cells in a dose-dependent manner, wherein the viability was determined by MTT assay. Meanwhile, the SLCB36 treatment did not significantly affect the cell viability.

Figure 8:
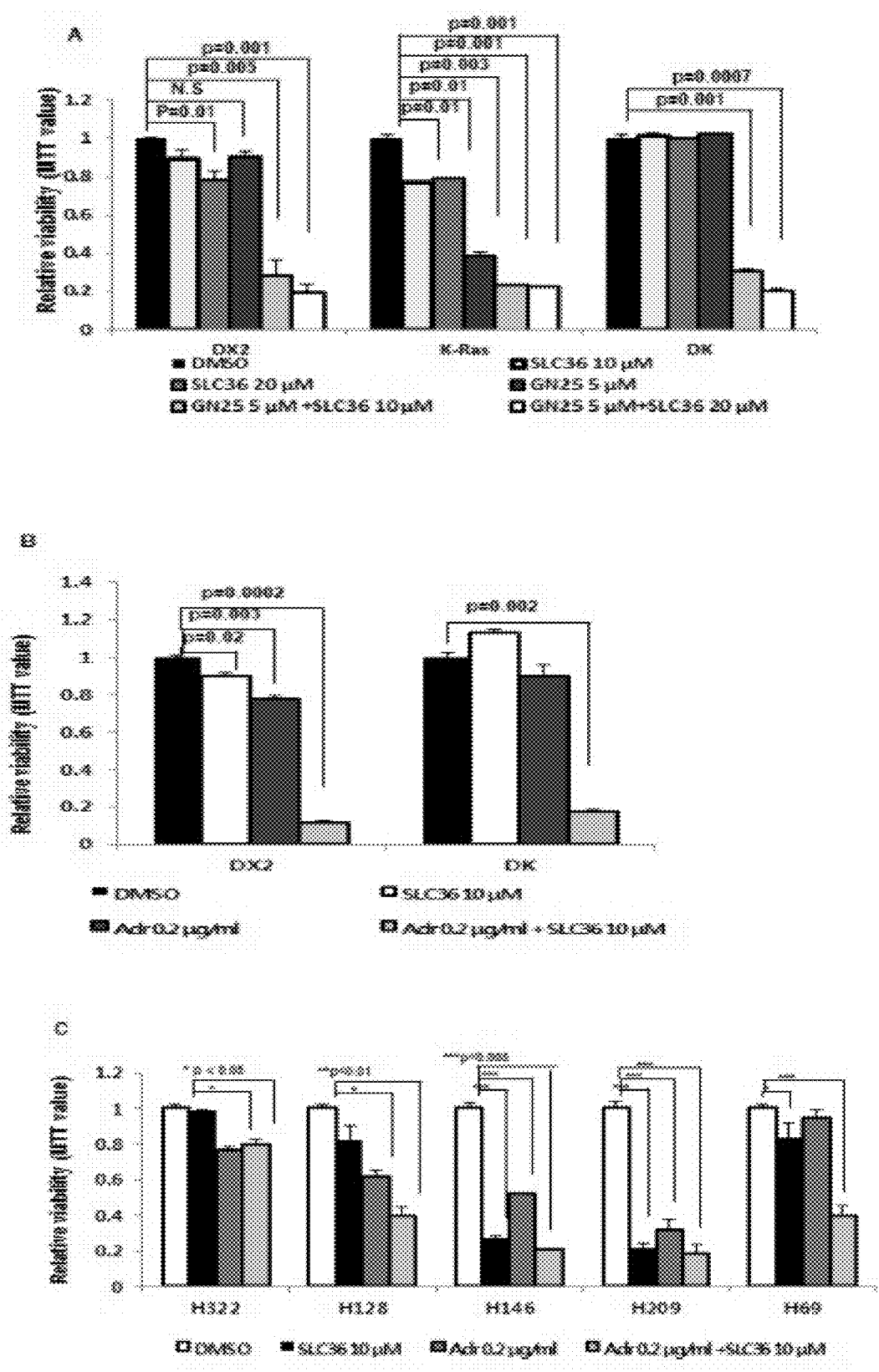
FIG. 8 shows effects of SLCB050 treatment on reduction of drug resistance of an anticancer drug.

FIG. 8 shows inhibitory effect of SLCB050 on drug resistance of an anticancer drug against DX2 expressed cells. FIG. 8A shows effects of SLCB050 on reduction of drug resistance of an anticancer drug when treated together with GN25 [5 μM, 3-(5,8-dimethoxy-1,4-dioxonaphthalene-2-ylthio)propanoic acid] and SLCB050 (10 or 20 μM), which are p53 activators, for 6 hours in DX2 and DK MEFs, wherein the effects were determined by MTT analysis. Here, resistance to GN25 in DX2 and DK cells was abolished by SLCB050 treatment, thereby recovering anticancer effects of GN25. FIG. 8B shows effects of SLCB050 on reduction of drug resistance of primary tumor cells from DX2 and DK mice when treated together with Adriamycin (0.2 μg/ml) and SLCB050 (10 μM) for 24 hours, wherein the effects were determined by MTT analysis. Here, resistance to Adriamycin was also abolished by SLCB050 treatment, thereby recovering anticancer effects of Adriamycin. FIG. 8C shows sensitivity of SCLC cell lines to combinational treatment with Adriamycin and SLCB050. Here, SCLC cell line H69 was partially responded to SLCB050 so that the sensitivity to Adriamycin improved, whereas p14/ARF-deficient H322 cells did not show improved sensitivity by combinational treatment with SLCB050.

Figure 9:
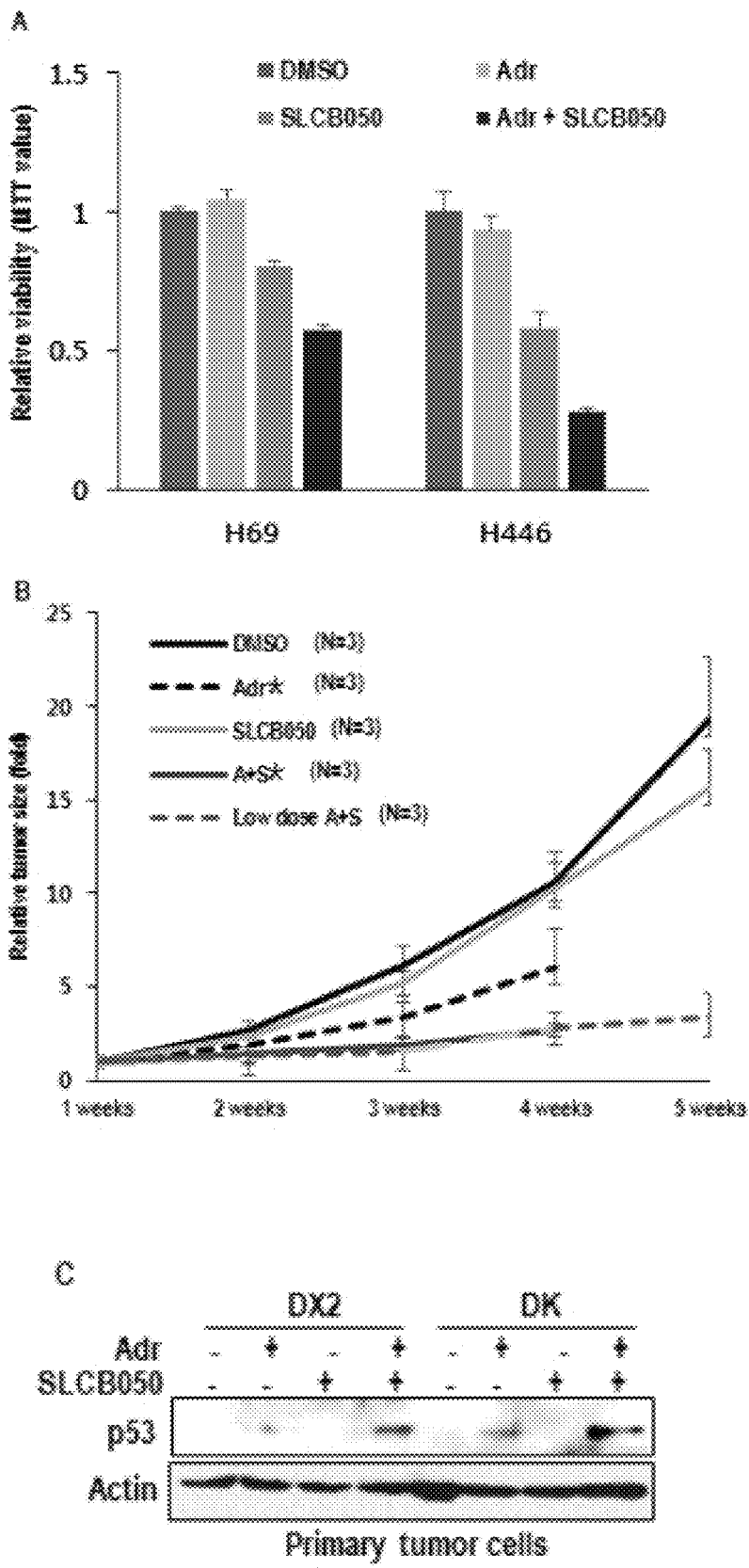
FIG. 9 shows inhibitory effects on drug resistance to Adriamycin in a xenograft model using H446 (Adr: 0.2 µg/ml, SLCB050: 10 mg/kg)

FIG. 9 shows inhibitory effects on drug resistance to Adriamycin in a xenograft model using H446. FIG. 9A shows resistance to Adriamycin in the xenograft model using H446, and also shows decreased resistance by SLCB050 treatment. FIG. 9B shows that tumor growth was suppressed within 4 weeks by treatment of 5 mg/kg of Adriamycin, but the experiment was ceased by high toxicity. In constrast, low dose of Adriamycin (2.5 mg/kg) with 10 mg/kg of SLCB050 obviously suppressed tumor growth without severe toxicity. FIG. 9C confirmed through Wester blotting that combinational treatment with Adriamycin and SLCB050 induced p53 synergistically in primary tumor cells.

Figure 10:
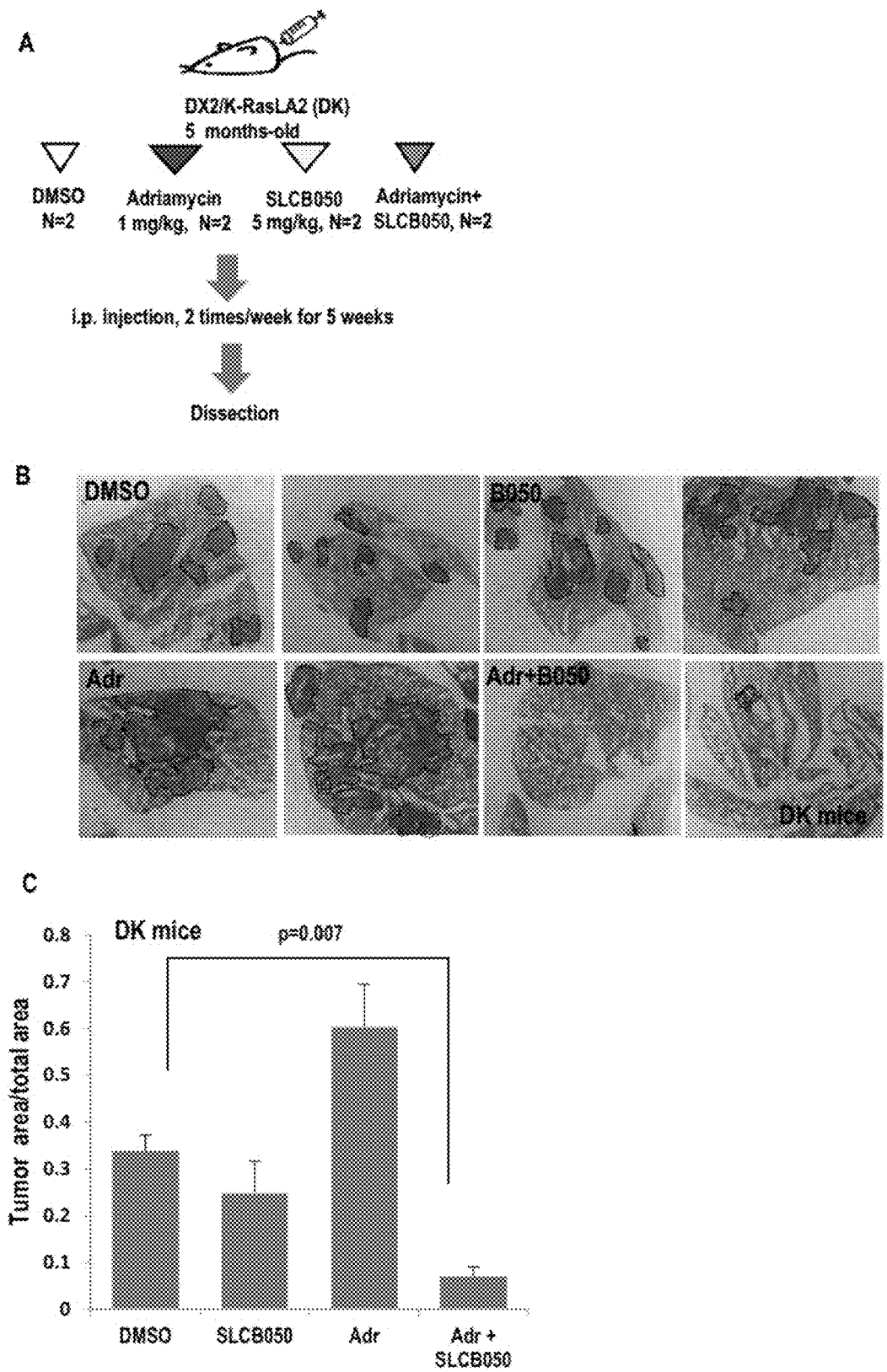
FIG. 10 shows in vivo anticancer effects of SLCB050.

FIG. 10 shows in vivo anticancer effects of SLCB050. FIG. 10A shows a diagram of experimental schedule with DK mice in terms of examination of in vivo anticancer effects. FIG. 10B shows hematoxylin-eosin (H-E) staining results of lung tissues derived from SLCB050-treated DK mice. Here, combinational treatment with Adriamycin and SLCB050 induced tumor regression. FIG. 10C shows that combinational treatment with Adriamycin and SLCB050 reduced tumor volumes.

Figure 11:
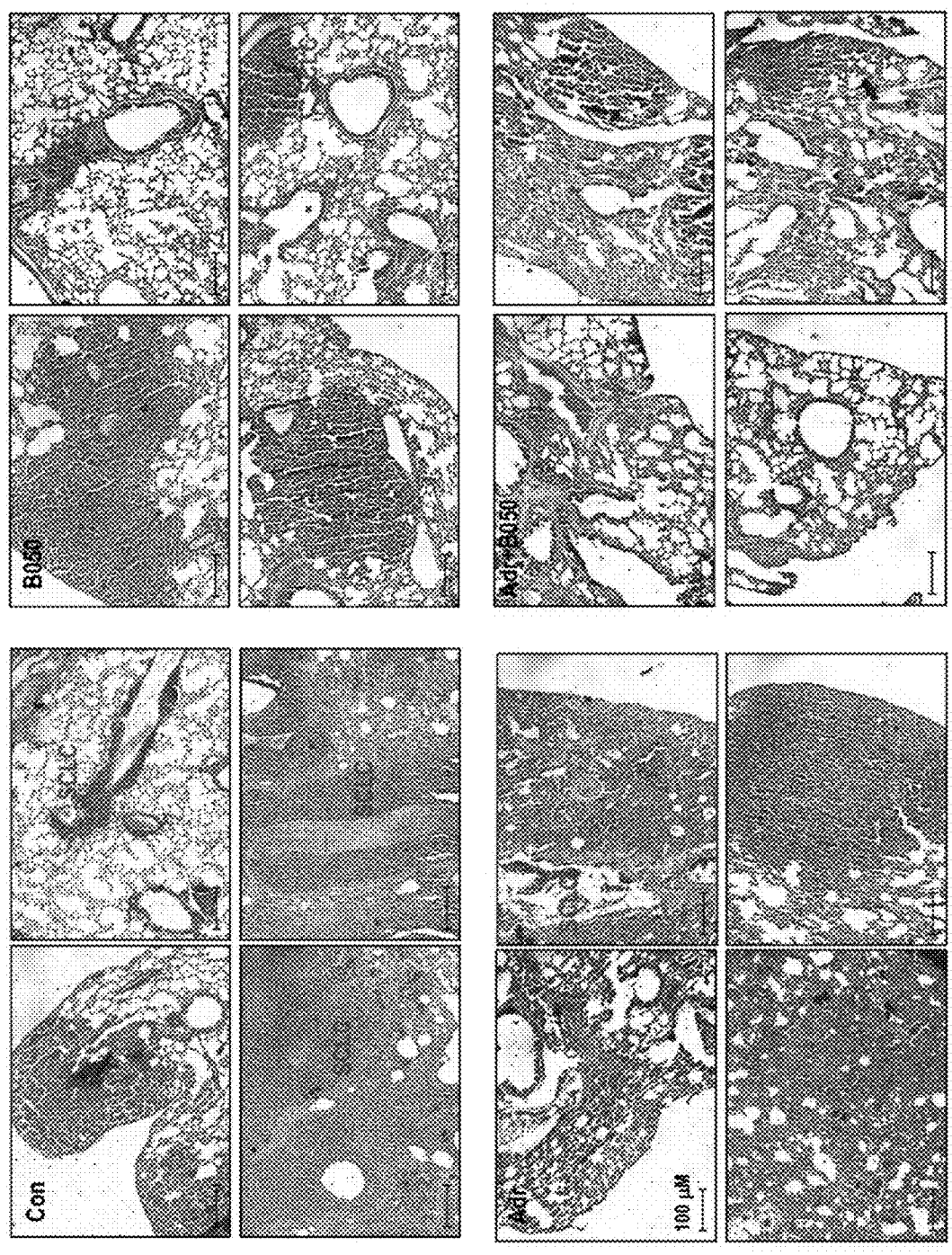
FIG. 11 shows hematoxylin-eosin (H-E) staining results of lung tissues derived from SLCB050-treated DK mice.

FIG. 11 shows H-E staining results of lung tissues derived from SLCB050-treated DK mice. Here, SCLC regions were more obviously erased by combinational treatment with Adriamycin and SLCB050.

Figure 12:
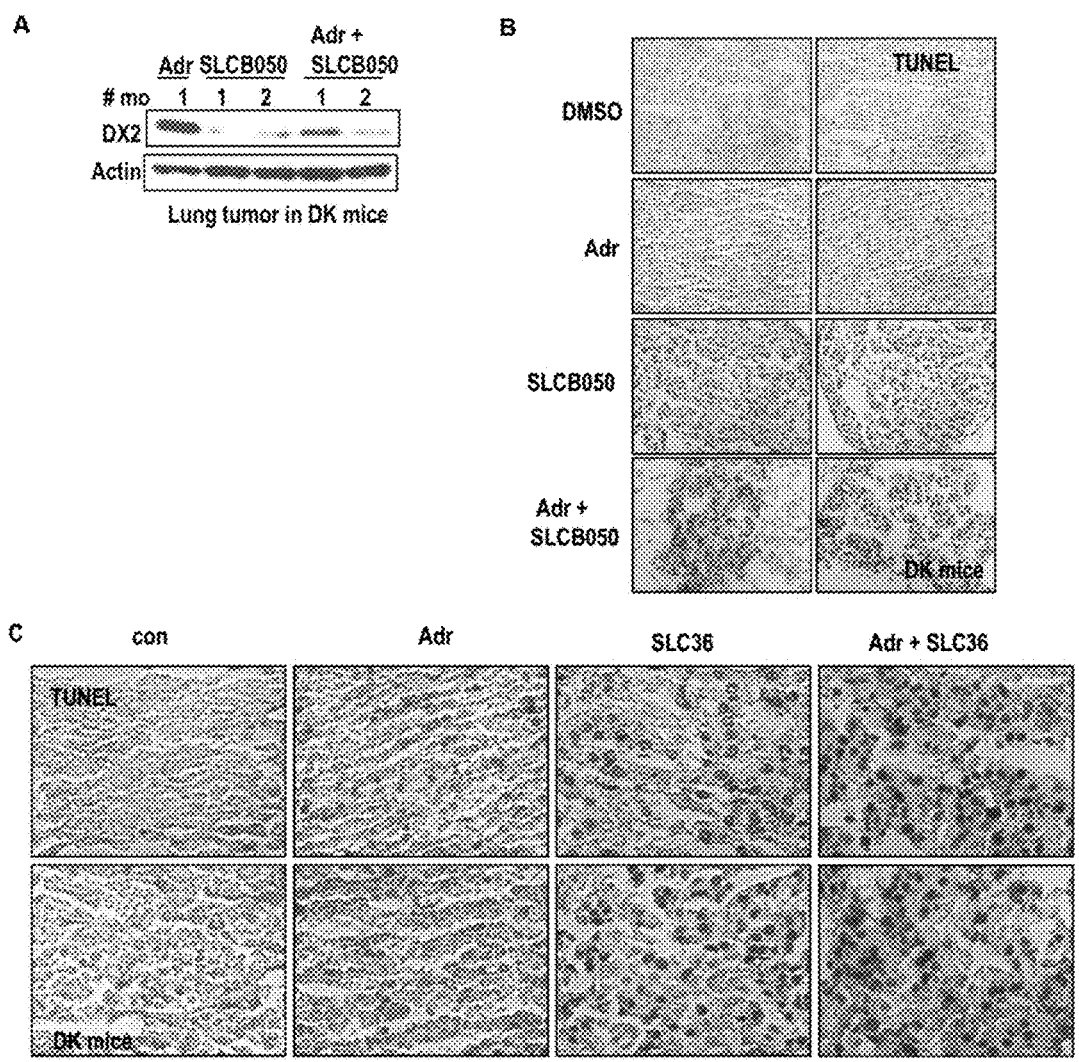
FIG. 12 shows in vivo anticancer effects of SLCB050.

FIG. 12 shows in vivo anticancer effects of SLCB050. FIG. 12A is a western blot analysis result showing reduction of DX2 in response to SLCB050 treatment. FIGS. 12B and 12C show TUNEL staining results from lung tissues of DK mice treated with Adriamycin and SLCB050 in combination. Here, SLCB050 treatment obviously increased apoptosis tumer cells.

Figure 13:
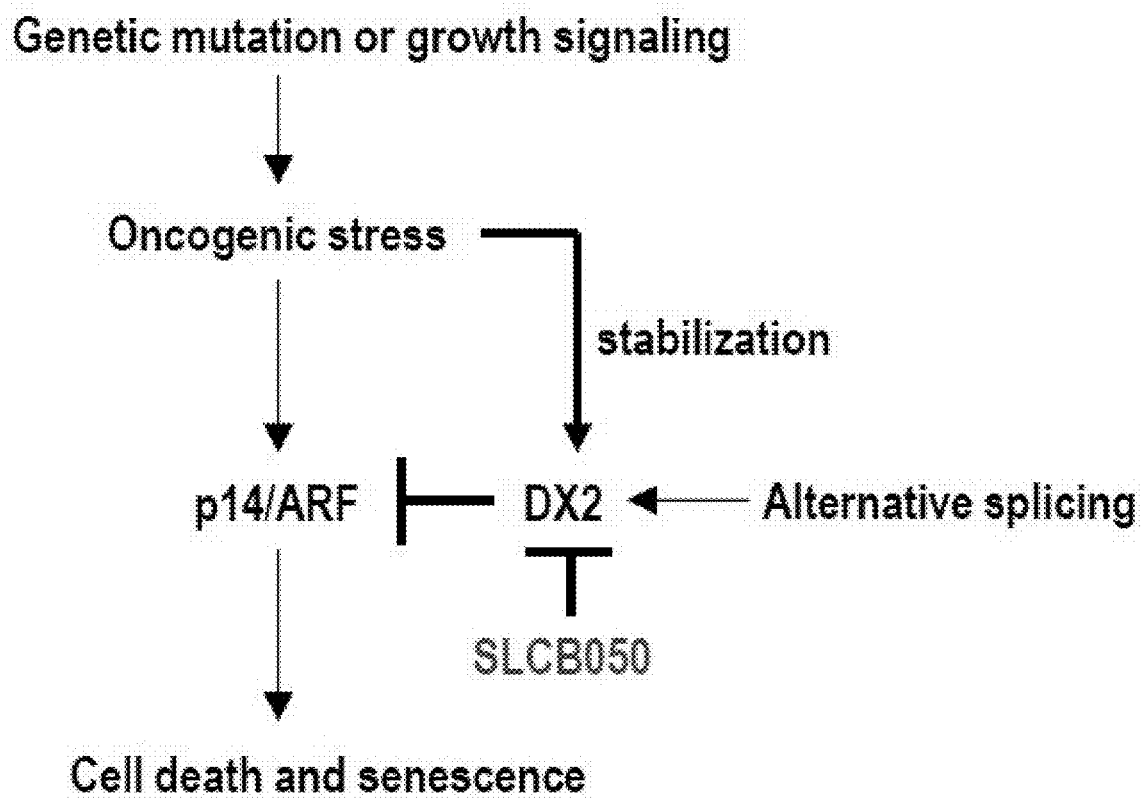
FIG. 13 shows the mechanism of SLCB050 of the present invention, which is a compound inhibiting DX2-p14/ARF binding, on therapeutic effect on lung cancer.

As shown in FIG. 13, the results above indicate that DX2 produced by aberrant splicing of AIMP2 promotes tumor progression, in particularly, small cell lung cancer, via direct interaction and inhibition of p14/ARF. In this regard, it was confirmed that such small cell lung cancer can be treated by using compounds that inhibit DX2-p14/ARF binding.

Accordingly, the present invention provides a pharmaceutical composition for treating or preventing a cancer disease, the pharmaceutical composition including, as an effective component, a compound represented by Formula 1, 2, or 3:

[Formula 1]

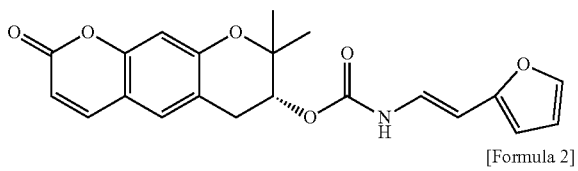

[Formula 2]

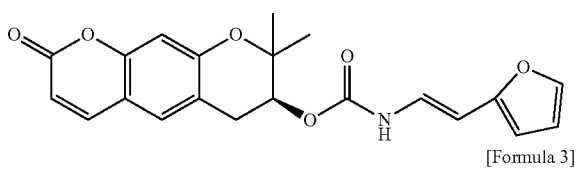

[Formula 3]

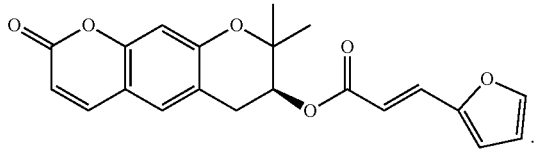

The compound above may inhibit binding between a DX2 protein and a p14/ARF protein.

The cancer disease may be selected from the group consisting of lung cancer, colorectal cancer, liver cancer, stomach cancer, esophageal cancer, pancreatic cancer, gallbladder cancer, kidney cancer, bladder cancer, prostate cancer, testis cancer, uterine cervical cancer, endometrial cancer, choriocarcinoma, ovarian cancer, breast cancer, thyroid cancer, brain cancer, head and neck cancer, malignant melanoma, lymphoma, and hematologic malignancy, and the lung cancer may be non small cell lung cancer or small cell lung cancer, and more preferable, may be small cell lung cancer.

In addition, the present invention provides a pharmaceutical composition for inhibiting drug resistance of an anticancer drug, the pharmaceutical composition including, as an effective component, a compound represented by Formula 1, 2, or 3.

The anticancer drug may be selected from the group consisting of Adriamycin, Capecitabine, Caboplatin, Cisplatin, Oxaliplain, Cyclophosphamide, Docetaxel, Paclitaxel, Doxorubicin, Daunorubicin, Epirubicin, Idarubicin, Valrubicin, Mitoxantrone, Curcumin, Gefitinib, Erlotinib, Irinotecan, Topotecan, Vinblastine, Vincristine, Gemsitabin, Methotrexate, Trastzumab, Vinorelbine, Fluorouracil, and 3-(5, 8-dimethoxy-1,4-dioxonaphthalene-2-ylthio)propanoic acid.

The compound above may inhibit binding between a DX2 protein and a p14/ARF protein to thereby inhibit drug resistance of the anticancer drug and improve anticancer effect of the anticancer drug.

In addition, the present invention provides a pharmaceutical composition for treating or preventing a cancer disease, the pharmaceutical composition including, as effective components, a compound represented by Formula 1, 2, or 3 and an anticancer drug.

The anticancer drug may be selected from the group consisting of Adriamycin, Capecitabine, Caboplatin, Cisplatin, Oxaliplain, Cyclophosphamide, Docetaxel, Paclitaxel, Doxorubicin, Daunorubicin, Epirubicin, Idarubicin, Valrubicin, Mitoxantrone, Curcumin, Gefitinib, Erlotinib, Irinotecan, Topotecan, Vinblastine, Vincristine, Gemsitabin, Methotrexate, Trastzumab, Vinorelbine, Fluorouracil, and 3-(5,8-dimethoxy-1,4-dioxonaphthalene-2-ylthio)propanoic acid, lung cancer, colorectal cancer, liver cancer, stomach cancer, esophageal cancer, pancreatic cancer, gallbladder cancer, kidney cancer, bladder cancer, prostate cancer, testis cancer, uterine cervical cancer, endometrial cancer, choriocarcinoma, ovarian cancer, breast cancer, thyroid cancer, brain cancer, head and neck cancer, malignant melanoma, lymphoma, and hematologic malignancy, and the lung cancer may be non small cell lung cancer or small cell lung cancer, and more preferable, may be small cell lung cancer.

The pharmaceutical composition may include, as a specific inhibitor against binding between DX2 and p14/ARF, not only screened compounds, SLCB050, HJH141204, and HJH141206, but also a pharmaceutically acceptable carrier of the screened compounds, in an effective amount. The term "effective amount" as used herein refers to an amount sufficient to exhibit therapeutic effects on cancer.

The pharmaceutically acceptable carrier included in the pharmaceutical composition of the present invention may be any material conventionally used at the time of formulation, and examples thereof include a carbohydrate compound (e.g., lactose, amylase, dextrose, sucrose, sorbitol, mannitol, starch, cellulose, etc), Acacia rubber, calcium phosphate, alginate, gelatin, calcium silicate, microcrystalline cellulose, polyvinylpyrrolidone, cellulose, water, syrup, salt solution, alcohol, gum Arabic, vegetable oil (e.g., corn oil, cotton seed oil, soybean oil, olive oil, coconut oil, etc), polyethylene glycol, methyl cellulose, methylhydroxybenzoate, propylhydroxybenzoate, talc, magnesium stearate, and mineral oil. But the examples of the pharmaceutically acceptable carrier re not limited thereto.

The pharmaceutical composition according to the present invention may further include, in addition to the components described above, a lubricant, a wetting agent, a sweetener, a flavoring agent, an emulsifying agent, a suspending agent, or a preservative. Materials suitable as the pharmaceutically acceptable carrier and formulation are provided in detail in Remington's Pharmaceutical Sciences (19th ed., 1995).

The pharmaceutical composition according to the present invention may be administered orally or parenterally. In the case of parenteral administration, the administration may be done via intravenous injection, subcutaneous injection, or muscle injection.

A suitable dose of the pharmaceutical composition according to the present invention may vary depending on various factors such as a method for formulation, a method for administration, a patient's age, weight, sex, disease condition, or diet, administration time, an administration route, an excretion rate, and responsiveness. In general, a skilled doctor may readily determine and prescribe an effective dose in terms of desired treatment or prophylaxis. According to a preferable embodiment of the present invention, the dose of the pharmaceutical composition may be 0.0001 to about 100 mg/kg (body weight) per day, and it may be administered once or several times per day.

The pharmaceutical composition according to the present invention may be prepared according to a method that can be easily carried out by those skilled in the art. For example, the pharmaceutical composition may be prepared in unit dosage form by formulation with a pharmaceutically acceptable carrier and/or excipient. Alternatively, the pharmaceutical composition may be prepared in a multi-dose container. Here, a formulation of the pharmaceutical composition may be oil or solution in an aqueous medium, suspension or emulsion, extract, powder, granule, tablet, or capsule, and may further include a dispersant or a stabilizer.

The present invention provides a composition for diagnosing lung cancer, the composition including AIMP2-DX2 protein or a fragment thereof.

Autoantibodies to AIMP2-DX2 are produced in a patient with lung cancer, especially with small cell lung cancer. In this regard, detection of autoantibodies enables diagnose of lung cancer. As a representative method of detecting the autoantibodies, target proteins to be antigens are immobilized on a fixture to be then reactive with a blood or serum sample including antibodies extracted from a subject, thereby confirming the presence of binding between the autoantibodies and the sample.

The inventor of the present invention discovered the production of autoantibodies to AIMP2-DX2 in a patient with lung cancer, and confirmed whether autoantibodies to AIMP2-DX2 are found in serum of a subject after immobilizing AIMP2-DX2 on a fixture for reaction with serum of the subject. Here, autoantibodies to AIMP2-DX2 were not detected in serum of a healthy person while the autoantibodies were detected in a patient with SCLC or NSCLC.

Therefore, AIMP2-DX2 or a fragment thereof may be used for diagnosis of lung cancer. AIMP2-DX2 may be a deletion variant of AIMP2 lacking exon 2 from the AIMP2 sequence, and ARS-interacting multi-functional protein 2 (AIMP2) is one of proteins related to formation of an aminoacyl-tRNA synthetase (ARS) composite, and is also referred to as p38/JTV-1 or p38.

The inventor of the present invention discovered in a previous study that, in terms of a new function of AIMP2, genetic collapse of AIMP2 induced overexpression of c-myc and accordingly caused hyperproliferation of alveolar epithelial cells in lungs, thereby inducing neonatal lethality of neuronal mice. In addition, the inventor of the present invention discovered that AIMP2 induced by TGF-β moves to the nucleus for inhibition of expression based on molecular and cytological analysis (M. J. Kim, B.-J. Park, Y.-S. Kang, H. J. Kim, J.-H. Park, J. W. Kang, S. W. Lee, J. M. Han, H.-W. Lee, S. Kim, Nat. Genet. 34, 330-336, 2003).

AIMP2-DX2 of the present invention may be a deletion variant of AIMP2 lacking exon 2 from the AIMP2 sequence. The AIMP2 sequence is found in several databases (312aa version:AAC50391.1 or GI:1215669; 320aa version: AAH13630.1, GI:15489023, BC013630.1) and publications (312aa version: Nicolaides, N. C., Kinzler, K. W. and Vogelstein, B. Analysis of the 5' region of PMS2 reveals heterogeneous transcripts and a novel overlapping gene, Genomics 29 (2), 329-334 (1995)//320 aa version: Generation and initial analysis of more than 15,000 full-length human and mouse cDNA sequences, Proc. Natl. Acad. Sci. U.S.A. 99 (26), 16899-16903 (2002)). AIMP2-DX2 is a protein lacking a region corresponding to exon 2 in the sequence. KR 2004-0078035 disclosed by the same inventor of the present invention discloses cancer therapy efficacy of AIMP2, and the description of AIMP2 in this patent document is incorporated herein by reference.

AIMP2-DX2 protein may include a protein lacking exon 2 from the whole AIMP2 sequence, and in this regard, may also include a protein lacking exon 2 from AIMP2 equivalents (functional equivalents that are variants resulting from substitution, deletion, insertion, or a combination thereof of the AIMP2 amino acid sequence, but have substantially equivalent activity to AIMP2, or functional derivatives that have modifications that enhance or reduce physicochemical properties or having substantially equivalent activity to AIMP2) is deleted.

AIMP2-DX2 protein may include a protein in which the amino acid sequence spanning exon 2 in AIMP2 wholly deleted, a protein including the amino acid sequences of exon 2 so that only a part of the amino acid sequence spanning exon 2 is deleted from exon 1, exon 3, exon 4, or all of these exons, a protein in which the amino acid sequence of exon 2 in AIMP2 is partially deleted. Preferably, AIMP2-DX2 of the present invention may include a protein in which the amino acid sequence spanning exon 2 in AIMP2 is wholly deleted.

AIMP2-DX2 protein of the present invention may include not only a protein having natural-occurring amino acid sequences, but also a variant of modified sequences. The variant of AIMP2-DX2refers to a protein having a different sequence from a natural-occurring amino acid sequence of AIMP2-DX2 prepared by deletion, insertion, non-conserved or conserved substitution, or a combination thereof. The alteration of amino acids in proteins and peptides where molecular activity is not substantially impaired is well known in the art. The most common alternation includes alternation between amino acid residues Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly.

In some cases, AIMP2-DX2 protein may be subjected to modifications such as phosphorylation, sulfation, acrylation, glycosylation, methylation, and farnesylation.

The fragment of AIMP2-DX2 protein of the present invention refers to a peptide or protein including a part of the amino acid sequences of AIMP2-DX2 protein. Then, any material having a part of AIMP2-DX2 amino acid sequence and a structure allowing binding of an antibody specifically to AIMP2-DX2 protein may be used as the fragment of AIMP2-DX2 protein.

AIMP2-DX2 or a fragment thereof may be naturally extracted, synthesized, or prepared by recombinant methods based on DNA sequences. When a recombinant DNA technology is used, a suitable expression vector carrying a nucleic acid encoding AIMP2-DX2 was transformed to a recombinant expression vector, and a host cell was cultured with the transformant to allow expression of AIMP2-DX2, thereby covering AIMP2-DX2 from the transformant.

Preferably, AIMP2-DX2of the present invention may include an amino acid sequence of SEQ ID NO: 5 or 6.

The lung cancer of the present invention may include both non small cell lung cancer (NSCLC) and (small cell lung cancer (SCLC), and preferably, the lung cancer of the present invention may include SCLC.

The present invention provides a method of detecting anautoantibody to AIMP2-DX2 protein to provide information for lung cancer diagnosis, the method including: (a) detecting an antibody to AIMP2-DX2in a sample derived from a subject; and (b) determining that a subject has lung cancer or is susceptible to lung cancer in the case when an amount of the detected antibody in the sample is greater than that in a normal person.

Hereinafter, the method of the present invention will be described step by step.

(a) Detecting an Antibody to AIMP2-DX2from a Sample Derived From a Subject

In step (a), an antibody to AIMP2-DX2 protein is detected from a sample derived from a subject.

The sample derived from the subject refers to a substance extracted from a person desire to confirm whether the person has lung cancer, and types of the substance are not particularly limited.

The sample of the present invention refers to, for example, a composition obtained or derived from a subject desire to confirm whether the person has lung cancer, the composition including autoantibodies that can be identified based on physical, biochemical, or physiological characteristics.

The sample may include blood of biological origin and other liquid and tissue samples. The source of the tissue sample may include fresh, frozen, and/or preserved organs or tissue samples, solid tissues from biopsy or aspiration, blood, any blood component, body fluid, and cells or serum from any time during pregnancy or embryogeny of a subject. The sample of the present invention may include whole blood, blood-derived cells, serum, plasma, lymph, synovia, cell extract, and a combination thereof, but is not limited thereto. Preferably, the sample may include serum, plasma or serum, or more preferably, serum.

The antibody may be against AIMP2-DX2 protein, and more preferably, may be an anti-AIMP2-DX2 autoantibody, and more preferably, may be an anti-AIMP2-DX2 IgG.

The detecting of the antibody to AIMP2-DX2 may be preferably made by antigen-antibody binding. That is, an antibody specifically binds to epitopes which are two-dimensional to three-dimensional parts of an antigen. Therefore, if an antigen and an antibody are able to bind to each other immunologically, it is said that the antigen and the antibody are "specific", "recognizable", or "bound". The antigen may be preferably AIMP2-DX2 protein or a fragment thereof.

The detecting of the antibody of the present invention may be performed by any known method of detecting the presence of antibody. However, such a known method may be heterogeneous or homogeneous, sequential or simultaneous, or competitive or non-competitive. The detecting of the antibody of the present invention may be performed in a quantitative manner to test a concentration or amount of anti-AIMP2-DX2 autoantibody. Alternatively, the detecting of the antibody of the present invention may be performed in a qualitative manner to test the presence of anti-AIMP2-DX2 autoantibody.

Preferably, the step (a) of detecting the antibody to AIMP2-DX2from the sample derived from the subject may include: (a1) applying the sample derived from the sample to a fixture on which AIMP2-DX2or a fragment thereof is immobilized to allow a reaction; and (a2) detecting antibodies bound to AIMP2-DX2in the reaction product.

The detecting of the antibody of the present invention may be performed by both binding between a non-immobilized antigen and an antibody and binding between an immobilized antigen and an antibody, but more preferably, may be performed by binding between a non-immobilized antigen and an antibody.

That is, after AIMP2-DX2(antigen) that is specifically reactive to an anti-AIMP2-DX2 autoantibody is bound to a fixture (solid support), the sample derived from the subject is mixed the reaction product to test the presence of the anti-AIMP2-DX2 antibody. Here, the antigen which is in a bound state with the fixture is in contact with a biological sample which is an unbound state, thereby forming antigen-antibody binding. Afterwards, the fixture is washed so that the reaction sample including antibodies that are not bound to immobilized antigens is removed. After completion of such treatments, an immune complex of the antigen and the anti-AIMP2-DX2 antibody is formed.

The detection of the present invention may be performed by, more preferably, a sandwich assay including procedures of adding a secondary antibody conjugate labeled with a detectable marker (for example, anti-human IgG antibody) to form a sandwich-type antigen-antibody complex through induction of binding between the secondary antibody conjugate and the immune complex and identifying the detectable marker conjugated to the secondary antibody bound to the sandwich-type antigen-antibody complex.

The secondary antibody may include an immunoglobulin fragment prepared by recombination with natural immunoglobulines isolated from non-human primates (e.g., anti-human IgG mouse antibody, anti-human IgG goat antibody, etc) or by synthesis.

The marker conjugated to the secondary antibody may be, preferably, a conventional coloring agent that performs a color reaction, and examples of the marker include a fluorescein, such as horseradish peroxidase (HRP), alkaline phosphatase, coloid gold, poly L-lysine-fluorescein isothiocyanate (FITC), and Rhodamine-B-isothiocyanate (RITC), and a dye.

The sandwich assay was disclosed in U.S. Pat. No. 5,876,935, and identifying of the detectable marker conjugated to the secondary antibody may be performed by conventional methods such as enzyme-linked immunosorbent assay (ELISA), radioimmnoassay (RIA), sandwich assay, western blotting on polyacrylamide gel, immunoblotting analysis, or immnohistochemical staining.

As the fixture of the present invention, any solid support widely used as a means for immobilizing AIMP2-DX2or its fragment may be used. Examples of suitable materials for use as the fixture include synthetic materials, such as polystyrene, polyvinylchloride, and polyamide, and other synthetic polymers. In addition, such materials may include natural polymers, such as cellulose, or may be derived from natural polymers, such as cellulose acetate, nitrocellulose, and glass. The fixture may be in form of ball, branch, tube, and microassay or microtiter plate. In addition, such materials may have a sheet-type structure, such as a paper strip, a small plate. And a membrane.

(b) Determining That a Subject Has Lung Cancer or is Susceptible to Lung Cancer in the Case When an Amount of the Detected Antibody in the Sample is Greater Than That in a Normal Person In step (b), a subject with an increased amount of antibodies detected in step (a) as compared with an amount of anti-AIMP2-DX2 antibodies in a normal person is determined to have lung caner or be susceptible to lung cancer.

The amount of antibodies detected in step (a) refers to an amount of antibodies to AIMP2-DX2 protein in the sample, i.e., an amount of antu-AIMP2-DX2 autoantibodies.

The anti-AIMP2-DX2 autoantibodies are not detected in a normal person who does not have lung cancer, but are detected in a patient with lung cancer. In particular, the anti-AIMP2-DX2 autoantibodies are significantly highly detected in a patient with SCLC.

Therefore, when the level of autoantibodies to AIMP2-DX2 protein detected in a sample of a subject is higher that of autoantibodies detected in a sample of a normal person, the target subject may be determined to have lung cancer or to be highly susceptible to lung cancer.

Referring to the steps described above, the method of detecting autoantibodies to AIMP2-DX2 protein of the present invention may provide information for lung cancer diagnosis to the target subject.

According to an embodiment of the present invention, various SCLC and NSCLC cell lines were incubated, and transcription and expression levels of AIMP2-DX2 were measured. As a result, the transcription and expression of AIMP2-DX2 in SCLC and NSCLC cell lines were confirmed without a difference in levels.

According to an embodiment of the present invention, serum of a patient with SCLC and NSCLC was ensured to measure an amount of anti-AIMP2-DX2 antibodies in the serum by using a nitrocellulose membrane to which AIMP2-DX2 protein is attached. Consequently, it was confirmed that the anti-AIMP2-DX2 antibodies were not detected in a control group including serum of a healthy person, whereas the anti-AIMP2-DX2 antibodies were detected in a patient with SCLC and NSCLC. In particular, in the case of a patient with SCLC, it was confirmed that the anti-AIMP2-DX2 antibodies are significantly highly detected.

Meanwhile, the present invention provides a kit for diagnosing lung cancer, the kit including AIMP2-DX2 protein its a fragment.

The kit of the present invention may include AIMP2-DX2 protein or its fragment, detect antibodies to AIMP2-DX2 protein in the sample, and enable to diagnose lung cancer of a subject.

The kit of the present invention is characterized by including AIMP2-DX2 protein or a fragment thereof, and preferably, may be provided in a fixed conditionon a fixture (solid support) on which AIMP2-DX2or its fragment can be fixed. The fixture may be the same as defined above.

In addition, the kit of the present invention may specifically bind to an autoantibody binding to AIMP2-DX2, and may further include a secondary antibody conjugate to which a detectable marker is conjugated. The secondary antibody may be an antibody binding to an autoantibody (anti-AIMP2-DX2 antibody), and preferably, may be an anti-human IgG antibody. The detectable marker may be the same as defined above.

In addition, the kit of the present invention may further include an anti-AIMP2-DX2 autoantibody with a known amount in advance. Such anti-AIMP2-DX2 autoantibody with a known amount in advance may be used to establish a standard curve for measurement of an amount of an anti-AIMP2-DX2 autoantibody with an unknown amount in a sample derived from a subject.

In addition, the kit of the present invention may include a suitable substrate in terms of an antigen-antibody reaction and color development of the marker, a buffer, or the like.

Hereinafter, the present invention will be described in detail by explaining preferred embodiments of the invention. However, the preferred embodiments should be considered in descriptive sense only and not for purposes of limitation. Embodiments of the invention are provided to more fully describe the present invention to one of ordinary skill in the art.

EXAMPLE 1

Screening of an Inhibitor of DX2-p14/ARF Binding

The present invention is on the basis of KR 2014-0113543 disclosed by the inventor of the present invention. Considering that DX2 inhibits induction of carcinogen-inducible p14/ARF so that a specific binding inhibitor of DX2 and p14/ARF can be used as an anticancer drug, an anticancer drug was screened as follows.

1. Preparation of Compound Library

Compounds that were individually synthesized and natural compound library were prepared according to the related document (*J. Clin. Oncol.* 16, 1207-1217, 1998; *Nat. Rev. Cancer* 2, 489-501, 2002), and 8,000 compounds were provided from Korea Chemical Bank for the present experiments.

2. ELISA Analysis

To screen DX2-p14/ARF binding inhibitors, the screening system based on ELISA modified as shown in FIG. 1 was used. That is, 0.5% His-DX2 recombinant proteins were immobilized on a 96-well plate with paraformaldehyde (PFA). After performing drying and cleaning processes, GST-p14/ARF proteins were allowed to react with a random compound (final concentration: 0.1 mM). After 1 hour, the plate was washed using TBS-T, and then, incubated with anti-GST antibodies (1:10,000, 30 minutes) and anti-mouse-IgG-HRP (1:50,000, 1 hour). After performing a washing process twice, the plate was incubated with 3,3',5,5'-tetramethylbenzidine (TMB) solution (Calbiochem) and stop solution (1N $H_2SO_4$) for a reaction. Afterwards, by using an ELISA reader, values were measured at 450 nm, thereby selecting candidate dugs as DX2-p14/ARF binding inhibitors. Here, more detailed protocol for the present experiment is described in the known related document (*Nat. Rev. Cancer* 2, 489-501, 2002), and PAK1-Smad4 binding inhibitors were used to exclude drugs that are confirmed as common inhibitors.

3. Recombinant Proteins, Immunoprecipitation, and GST Pull-Down Assays

Through GST pull-down assays, more specific binding inhibitors were selected among the previously screened candidate drugs as DX2-p14/ARF binding inhibitors. That is, a p14/ARF fragment (full-length) was ligated into EcoRI and Hind II sites of pGEX-TEV vector, which is a modified vector by adding a TEV protease cleavage site to pGEX-4T1. The recombinant proteins were then expressed in *E. coli* strain BL21(DE3) as GST-fusion proteins. The proteins were purified by glutathione affinity chromatography.

To address direct binding between the two proteins, agarose-bead conjugated GST (negative control) or GST-target protein was incubated with cell lysate or recombinant protein in radioimmunoprecipitation assay (RIPA) buffer (NaCl, 25 mM Tris-Cl, 1% NP-40, 1% sodium deoxycholate, 0.1% SDS, protease inhibitor mixture) for 1 hour at a temperature of 4° C. for a reaction.

Immunoprecipitation (IP) assay was performed with cell lysate or recombinant protein with RIPA buffer. The whole lysates were incubated with suitable antibodies for 2 hours at a temperature of 4° C. for a reaction, and then, the mixtures were added with A/G-agarose beads-conjugated secondary antibody (Invitrogen, Carlsbad, Calif., USA) for 2 hours. After incubation for a reaction, the mixtures were washed using RIPA buffer twice, and precipitated proteins were determined by wester blot analysis.

4. Western Blot Analysis

To carry out western blot analysis, proteins were thermally inactivated in RIPA buffer (heat treatment for 7 minutes at a temperature of 95° C.), and then, the resulting proteins were applied to SDS-PAGE, followed by western blot analysis according to a known method in the art (*J. Clin. Oncol.* 16, 1207-1217, 1998; *Nat. Rev. Cancer* 2, 489-501, 2002). Antibodies used herein, e.g., HA (sc-7392), His (sc-8036), GFP (sc-9996), GST (sc-138), Actin (se-1616), and p19/ARF (sc-32748), were purchased from Santa Cruz Biochnology, anti-p14/ARF (MAB3782) was purchased from Millipore, and FLAG-M2 and anti-C-Myc (M5546) were purchased from Sigma Aldrich. In addition, anti-AIMP2 was provided from Professor. Kim, Sung-Hoon (Seoul Nat. Univ.).

5. Screening of DX2-p14/ARF Binding Inhibitor

As shown in FIGS. 2A, 2B, and 3A, SLCB050 was obtained as a compound that selectively inhibits DX2-p14/ARF binding. In particular, SLCB050 only blocked the interaction of DX2 and AIMP2 as shown in FIG. 2C, but not on p53-AIMP2 or DX2 binding as shown in FIG. 3B, and p14/ARF as shown in FIG. 3C. In this regard, it was confirmed that SLCB050 would be interacted with DX2-specific region.

Synthesis of SLCB050 [(7S)-(+)-3-(2-Furanyl)-acrylic acid, 8,8-dimethyl-2-oxo-6,7-dihydro-2H, 8H-pyrano[3,2-g]chromen-7-yl-ester]

[Reaction Formula 1]

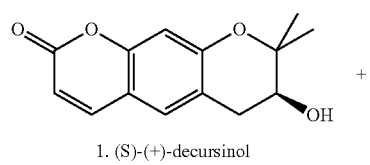

1. (S)-(+)-decursinol

+

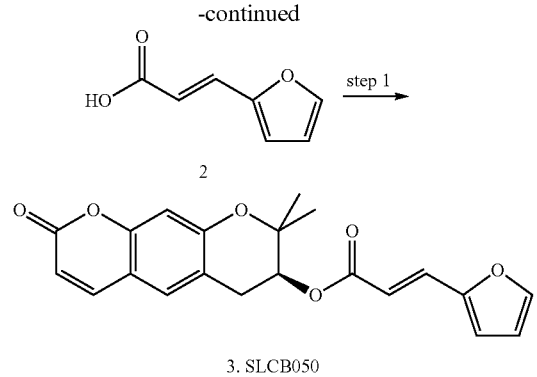

[Step 1]

Under $N_2$ gas, trans-3-(2-furanyl)acrylic acid (560 mg, 4.06 mmol, 1 eq), N-(3-dimethylaminopropyl)-N'-ethylcarbodiimide hydrochloride (EDC, 1.17 g, 6.09 mmol, 1.5 eq), and 4-(dimethylamino)pyridine (4-DMAP, 198 mg, 1.62 mmol, 0.4 eq) were added to a 100 mL round-bottom flask, and then, dissolved in anhydrous dichloromethane (100 ml). (S)-(+)-decursinol (1 g, 4.06 mmol, 1 eq, KR 0715206) was added to the mixed solution, followed by being stirred at room temperature for 5 hours and concentrated under reduced pressure. The filtrate was then separated by silica gel column (ethylacetate: n-hexane=gradient elution to 1:3 from 1:8), thereby obtaining (7S)-(+)-3-(2-furanyl)-acrylic acid, 8,8-dimethyl-2-oxo-6,7-dihydro-2H,8H-pyrano[3,2-g]chromen-7-yl-ester (SLCB050) having the following material properties:

yield: 73.6%; orange solid-phase; mp: 96.1° C.; $R_f$=0.62 (n-hexane:ethyl acetate=1:1); $[\alpha]_D^{25}$+62.4 (c=3, $CHCl_3$);

$^1$H NMR (400 MHz, $CDCl_3$): $\delta_H$ 7.64 (1H, s, H-6'), 7.58 (1H, d, J=9.6 Hz, H-4), 7.56 (1H, d, J=16.0 Hz, H-3'), 7.41 (1H, d, J=1.6 Hz, H-7'), 7.17 (1H, s, H-5), 6.82 (1H, s, H-10), 6.55 (1H, d, J=1.6 Hz, H-8'), 6.23 (1H, d, J=9.6 Hz, H-3), 6.13 (1H, d, J=16.0 Hz, H-2'), 5.17 (1H, t, J=4.4 Hz, H-7), 3.23 (1H, dd, J=4.4, 17.6 Hz, H-6a), 2.92 (1H, dd, J=4.4, 17.6 Hz, H-6b), 1.42 (3H, s, $CH_3$-8), 1.38 (3H, s, $CH_3$-8);

$^{13}$C NMR (100 MHz, $CDCl_3$) $\delta_C$ 166.3 (C-1'), 161.3 (C-2), 156.3 (C-9a), 154.1 (C-10a), 144.8 (C-4'), 144.5 (C-6'), 143.1 (C-4), 135.8 (C-3'), 128.7 (C-5), 117.0 (C-2'), 115.6 (C-5a), 113.3 (C-3), 112.9 (C-7'), 112.9 (C-4a), 107.2 (C-8'), 104.7 (C-10), 76.6 (C-8), 70.0 (C-7), 27.8 (C-6), 24.8 (CH3-8), 23.3 (CH3-8); and ESI-MS: m/z=389 [M+Na]$^+$.

6. Synthesis of HJH141204 and HJH141206

As analogous compounds to the previously screened SLCB050, HJH141204, HJH141206, and SLCB36 were each synthesized.

As shown in FIGS. 3D and 3E, SLCB050, HJH141204, and HJH141206 showed inhibitory effects on DX2-p14/ARF binding and did not affect the interaction of p53-p14/ARF, whereas SLCB36 did not show inhibitory effect on both binding. Accordingly, it was confirmed that inclusion of a ribose ring structure in the compounds is required for the binding inhibition.

1) Synthesis of HJH141206: (7S)-(+)-2-(Furan-2-yl)vinylcarbamic acid, 8,8-dimethyl-2-oxo-6,7-dihydro-2H,8H-pyrano[3,2-g]chromen-7-yl-ester

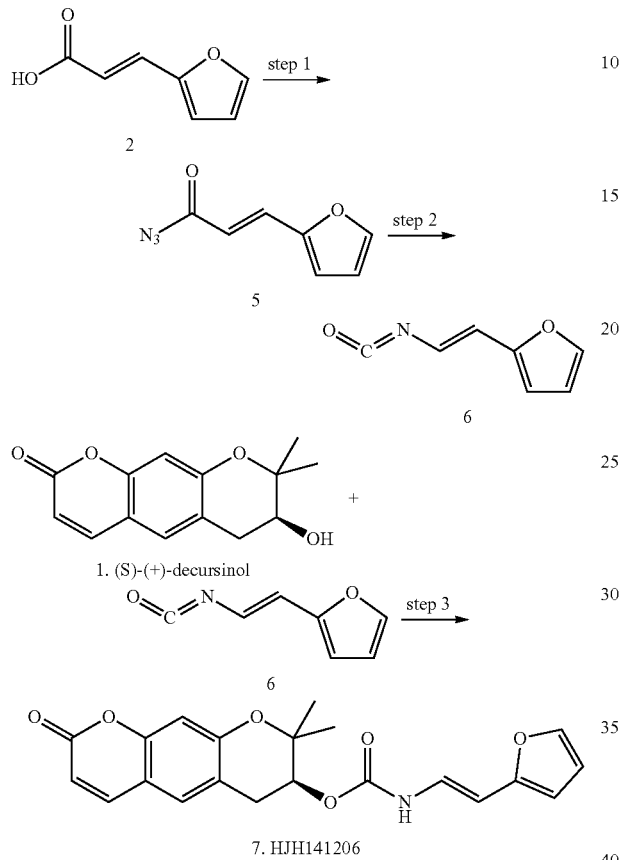

[Step 1] Trans-3-(2-furanyl)acrylic acid (500 mg, 3.37 mmol) was dissolved in 20 mL of dry benzene in a round-bottom flask, and then, triethyamine (TEA, 234 μl, 1.683 mmol) and diphenyl phosphoryl azide (DPPA, 362 μl, 1.683 mmol) were add thereto for a reaction at a temperature of 80° C. for 3 hours. After an extraction process using water and ethylacetate was performed on the mixed solution, a dehydration process using sodium sulfate was performed thereon, followed by being concentrated under reduced pressure.

[Step 2] The resulting product was dissolved again in dry benzene, and then, was heated to reflux at a temperature of 80° C. for one day.

[Step 3] (S)-(+)-decursinol (207 mg, 0.841 mmol) was added thereto, and TEA (281 μl, 2.019 mmol) and 4-(dimethylamino)pyridine (DMAP, 82 mg, 0.673 mmol) were also added thereto for a reaction at a temperature of 80° C. for 3 hours. The reaction solution was concentrated under reduced pressure, and the filtrate was then separated by silica gel column (ethylacetate: n-hexane=gradient elution to 1:3 from 1:8), thereby obtaining (7S)-(+)-2-(Furan-2-yl)vinylcarbamic acid, 8,8-dimethyl-2-oxo-6,7-dihydro-2H,8H-pyrano[3,2-g]chromen-7-yl-ester (HJH141206) having the following material properties:

yield: 69.7%; brown solid-phase; mp: 58.5° C.; $R_f$=0.46 (n-hexane:ethyl acetate=1:1); $[\alpha]_D^{25}$+79.6933 (c=3, CHCl$_3$);

$^1$H NMR (300 MHz, DMSO-d$_6$): δ$_H$ 9.894 (d, J=10.2 Hz, 1H), 7.920 (d, J=9.6 Hz, 1H), 7.493 (s, 2H), 6.984 (dd, J=10.2, 14.7 Hz, 1H), 6.798 (s, 1H), 6.401-6.383 (m, 1H), 6.264 (d, J=9.6 Hz, 1H), 6.190 (d, J=3.3 Hz, 1H), 5.912 (d, J=14.4 Hz, 1H), 5.056 (t, J=3.6 Hz, 1H), 3.254 (dd, J=4.2, 18.0 Hz, 1H), 2.917 (dd, J=3.3, 17.7 Hz, 1H), 1.384 (s, 3H, CH$_3$), 1.313 (s, 3H, CH$_3$);

$^{13}$C NMR (100 MHz, DMSO-d$_6$) δ$_C$ 160.3, 155.8, 153.5, 153.1, 151.5, 144.1, 141.1, 129.6, 123.9, 115.7, 112.7, 112.6, 111.5, 105.2, 103.5, 99.9, 76.8, 70.2, 27.3, 24.3, 23.7; and ESI-MS: m/z=382 [M+H]$^+$.

2) Synthesis of HJH141204: (7R)-(−)-2-(Furan-2-yl)vinylcarbamic acid, 8,8-dimethyl-2-oxo-6,7-dihydro-2H,8H-pyrano[3,2-g]chromen-7-yl-ester

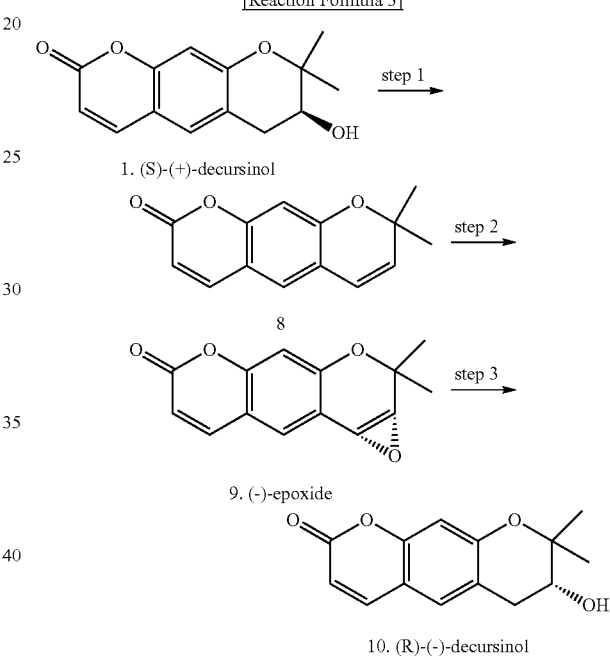

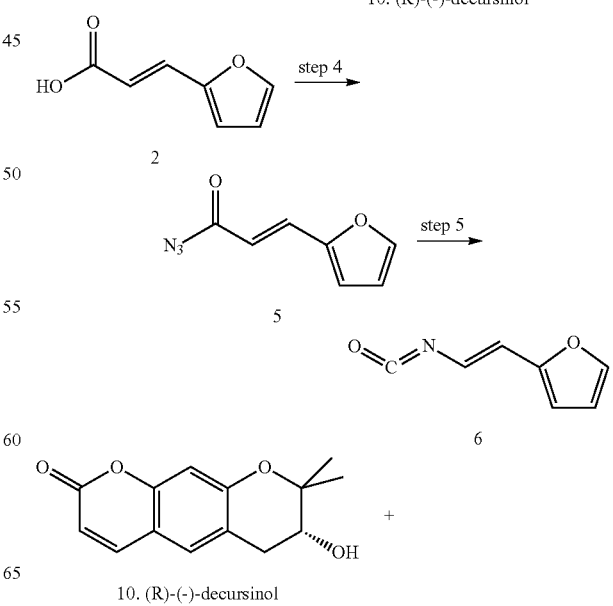

-continued

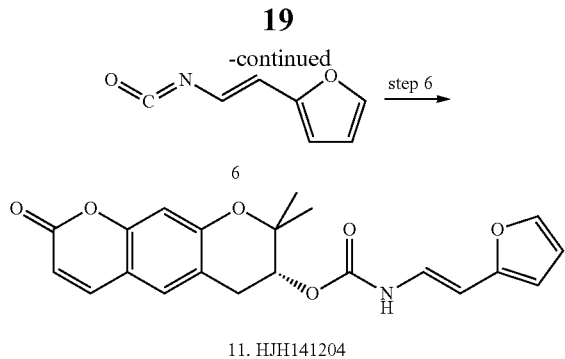

11. HJH141204

[Step 1] As shown in the reaction formula above, (+)-decursinol (1, 85 g, 0.35 mol) and triphenylphosphine (226 g, 0.87 mol) were added to a round-bottom flask, and acetonitrile (600 mL) and carbon tetrachloride (600 mL) were dissolved therein at a ratio of 1:1. Then, the mixed solution was refluxed at temperatures of 50-60° C. for 2 hours. About half of the filtrate was concentrated under reduced pressure, followed by being separated by silica gel column, thereby obtaining 8,8-domethyl-8H-pyrano[3,2-g]chromen-2-one(8) as a sample in the experiment having the following material properties:

yield: 98.6%; white solid-phase; m.p: 124° C.; $R_f$=0.62 (n-hexane:ethyl acetate=1:1);

$^1$H NMR (400 MHz, CDCl$_3$): $\delta_H$ 7.583 (d, J=9.52 Hz, 1H), 7.049 (s, 1H), 6.711 (s, 1H), 6.340 (d, J=10.0 Hz, 1H), 6.213 (d, J=9.52 Hz, 1H), 5.691 (d, J=9.76 Hz, 1H), 1.467 (s, 6H, CH$_3$X2); and ESI-MS: m/z=229 [M+H]$^+$.

[Step 2] 15% sodium hypochlorite (60 mL) and 0.05 M sodium phosphate dibasic (24 mL) were added to a round-bottom flask, and the reaction solution was adjusted using 1N sodium hydroxide solution or 1N hydrochloric solution to have pH of 11.3. Then, to the reaction solution, a solution in which 8,8-dimethyl-8H-pyrano[3,2-g]chromen-2-on (8, 1.3 g, 5.7 mmol) and (R,R)-(−),N,N'-bis(3,5-di-tert butyl-salicylidene)-1,2,-cyclohexanediamino manganese (III) chloride (Jacobsen catalyst, 69.9 mg, 0.11 mmol) were dissolved in dichloromethane (15 ml) was added. The mixed reaction solution was stirred at a temperature of 0° C. for about 7 hours. An extraction process was performed on the mixed reaction solution by using dichloromethane, and an organic layer obtained therefrom was washed with water, wherein the organic layer was reddish brown. After the organic layer was dried over anhydrous magnesium sulfate, the filtrate was concentrated under reduced pressure. To obtain pure products, the concentrated solution was separated by silica gel column, thereby obtaining (6R,7R)-6,7-epoxy-8,8-dimethyl-6H-pyrano[3,2-g]chromen-2-on(9) having the following material properties:

yield: 56.3%; white solid-phase; m.p: 145.2° C.; $R_f$=0.32 (n-hexane:ethyl acetate=1:1); [α]$_D^{25}$+201.8 (c=3, CHCl$_3$);

$^1$H NMR (400 MHz, CDCl$_3$): $\delta_H$ 7.643 (d, J=9.52 Hz, 1H), 7.470 (s, 1H), 6.754 (s, 1H), 1H), 6.265 (d, J=9.52 Hz, 1H), 3.976 (d, J=3.88 Hz, 1H), 3.551 (d, J=3.88 Hz, 1H), 1.609 (s, 3H, CH$_3$), 1.312 (s, 3H, CH$_3$); and ESI-MS: m/z=245 [M+H]$^+$.

[Step 3] As shown in the reaction formula above, (6R,7S)-6,7-epoxy-8,8-dimethyl-6H-pyrano[3,2-g]cyromen-2-on (9, 600 mg, 2.456 mmol) was dissolved in tetrahydrofuran in a round-bottom flask. Then, sodium cyanoborohydride and borane trifluoride diethyl etherate was added thereto. The mixed reaction solution was stirred at a temperature of 0° C. for 30 minutes. The filtrate of the mixed reaction solution was concentrated under reduced pressure, followed by being separated by silica gel column, thereby obtaining (−)-decursinol[decursinol; (7R)-7-hydroxy-8,8-dimethyl-8H-pyrano[3,2-g]chromen-2-on (10)] as a sample in the experiment having the following material properties:

yield: 98.6%; white solid-phase; m.p: 135.6° C.; $R_f$=0.179 (n-hexane:ethyl acetate=1:1); [α]$_D^{25}$−18.4 (c=4, CHCl$_3$);

$^1$H NMR (400 MHz, CDCl$_3$): $\delta_H$ 7.579 (d, J=9.5 Hz, 1H), 7.180 (s, 1H), 6.780 (s, 1H), 6.219 (d, J=9.52 Hz, 1H), 3.876 (d, J=5.1 Hz, 1H), 3.112 (dd, J=4.8 Hz, 16.7 Hz, 1H), 2.837 (dd, J=5.6 Hz, 16.6 Hz, 1H), 1.397 (s, 3H, CH$_3$), 1.367 (s, 3H, CH$_3$); and ESI-MS: m/z=247 [M+H]$^+$.

[Step 4] Trans-3-(2-furanyl)acrylic acid (500 mg, 3.37 mmol) was dissolved in 20 mL of dry benzene in a round-bottom flask, and then, TEA (234 μl, 1.683 mmol) and DPPA (362 μl, 1.683 mmol) were add thereto for a reaction at a temperature of 80° C. for 3 hours. After an extraction process using water and ethylacetate was performed on the mixed solution, a dehydration process using sodium sulfate was performed thereon, followed by being concentrated under reduced pressure.

[Step 5] The resulting product was dissolved again in dry benzene, and then, was heated to reflux at a temperature of 80° C. for one day.

[Step 6] (−)-decursinol (207 mg, 0.841 mmol) synthesized in step 3 was added thereto, and TEA (281 μl, 2.019 mmol) and 4-(dimethylamino)pyridine (DMAP, 82 mg, 0.673 mmol) was added thereto for a reaction at a temperature of 80° C. for 3 hours. The reaction solution was concentrated under reduced pressure, and the filtrate was then separated by silica gel column (ethyl acetate: n-hexane=gradient elution to 1:3 from 1:8), thereby obtaining (7R)-(−)-2-(Furan-2-yl)vinylcarbamic acid, 8,8-dimethyl-2-oxo-6,7-dihydro-2H,8H-pyrano[3,2-g]chromen-7-yl-ester (HJH141204) as a sample in the experiment having the following material properties:

yield: 80.9%; brown solid-phase; mp: 58.1° C.; $R_f$=0.46 (n-hexane:ethyl acetate=1:1); [α]$_D^{25}$−79.6467 (c=3, CHCl$_3$);

$^1$H NMR (300 MHz, DMSO-d$_6$): 9.896 (d, J=10.2 Hz, 1H), 7.902 (d, J=9.6 Hz, 1H), 7.477 (s, 2H), 6.992 (dd, J=10.2, 14.4 Hz, 1H), 6.790 (s, 1H), 6.396-6.387 (m, 1H), 6.255 (d, J=9.6 Hz, 1H), 6.185 (d, J=3.3 Hz, 1H), 5.919 (d, J=14.4 Hz, 1H), 5.059 (t, J=3.7 Hz, 1H), 3.251 (dd, J=4.2, 18.0 Hz, 1H), 2.922 (dd, J=3.3, 18.0 Hz, 1H), 1.384 (s, 3H, CH$_3$), 1.313 (s, 3H, CH$_3$);

$^{13}$C NMR (100 MHz, DMSO-d$_6$) $\delta_C$ 160.3, 155.9, 153.6, 153.2, 151.6, 144.0, 141.1, 129.6, 124.0, 115.7, 112.7, 112.6, 111.5, 105.2, 103.5, 100.0, 76.9, 70.3, 27.3, 24.3, 23.7; and ESI-MS: m/z=382 [M+H]$^+$.

3) SLCB36 Compound

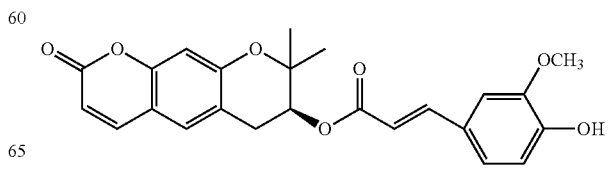

EXAMPLE 2

Evaluation of Anticancer Effect

1. Cell Culture

A549, HCT116, H1299, and HEK293 cell lines were each purchased from American Type culture collection (ATCC, Manassas, Va.), and cultured in RPMI-1640 medium or Dulbecco modified Eagle medium (DMEM) supplemented with 10% fetal bovine serum (FBS) and 1% antibiotics. NSCLC cell lines (NCI-H23, NCI-H322, NCI-H358, and NCI-H460) purchased from ATCC and SCLC cell lines (NCI-H69, NCI-H128m and NCI-H146) purchased from Korean Cell line Bank (KCLB, Seoul, Korea) were cultured in RPMI-1640 medium supplemented with 10% FBS. Mouse embryonic fibroblast (MEF) cells were isolated from 14.5 day embryos using a standard protocol and cultured in DMEM medium supplemented with 15% FBS and 1% antibiotics.

2. Preparation of Mice

All experimental procedures using laboratory animals were approved by the animal care committee of Pusan National University. DX2 (C57/BL6) and K-RasLA2 (C57/BL6) mice were obtained from Dr. Kim, Sung-Hoon and Professor. Choi, Kang-Ryeol (Yonsei University), respectively, and double Tg mice were obtained by cross-breeding of DX2 and K-RasLA2 mice. Before experiment, all mice were maintained under temperature- and light-controlled conditions (20-23° C., 12 h/12 h light/dark cycle), and provided autoclaved food and water.

3. Recombinant Proteins, Immunoprecipitation and GST Pull-Down Assays

In the same manner as in Example 1, recombinant proteins, IP assay, GST pull-down assay, and western blot analysis were performed.

4. MTT Assay

By MTT assay, anticancer effects were confirmed based on viability of tumor cells. That is, cells were incubated in 0.5 mg/ml of MTT solution for 4 hours at a temperature of 37° C. for a reaction, and then, formazen products formed therefrom were dissolved in dimethyl sulfoxide (DMSO). Then, absorbance thereof was measured at 540 nm by using a spectrometer.

5. Drug Treatment In Vivo

DK (5 month-old, N=6) mice were administered with carrier, SLCB050 (5 or 10 mg/kg), Adriamycin (1, 2.5, or 5 mg/kg), and a combination of SLCB050 and Adriamycin by intraperitoneal (i.p.) injection. After termination of the experiment of each group, mice were dissected and isolated lung tissues. For xenograft, 1×10⁷ H446 cells (ATCC) were seeded in nude ice. After 4 weeks, tumor bearing mice were injected with Adriamycin, SLCB0505, or a combination thereof for 6 weeks. Every weeks, tumor volume and body weight were measured.

6. Histological Analysis

After dissection of mice, tissues were fixed using 10% formalin (in PBS) for 24 hours, and embedded in paraffin blocks according to a basic tissue processing procedure. For histological analysis, embedded tissues were cut for 5 μM by Leica microtome (Wetzlar, Germany) and transferred onto adhesive-coated slides (Marienfeld laboratory glassware, Germany). After deparaffin and rehydration, sections were then stained with H&E for routine examination.

For IHC staining, rehydrated tissue sections were incubated with antibodies to Ki-67 (Abcam, ab15580), pan-keratin (Sigma, C2931), pro-surfactant C (Millipore, AB3786), NSE (DAKO, IS612), and HER2/Neu (DAKO, A0458) for a reaction. Antigen retrieval was performed using 10 mM sodium citrate (pH 6.0) twice at a temperature of 95° C. for 10 minutes each, and endogenous peroxidase activity was blocked with 3% hydrogen peroxidase for 10 min. Then, the slides were dehydrated following a standard procedure and sealed with cover glass using mounting solution. TUNEL reaction was done as described in the manual for In Situ Cell Death Detection Kit, POD (Hoffmann-La Roche Ltd, Basel, Swizerland).

7. Analysis of Tumor Incidence and Area

To evaluate tumor incidence, lung tissues of each mouse was fixed and embedded in paraffin. 5 sections from each mouse were examined by 3 independent investigator, who counted tumor. In addition, tumor area was calculated by tumor occupied area in total lung area using photoshop software.

8. Experiment Results

As shown in FIGS. 4A and 4B, SLCB050 treatment blocked the interaction of DX2-p14/ARF, and DX2 and p14/ARF were localized in nucleus. In addition, the increase of p14/ARF in SLCB050-treated H1299 and H69 cell lines was observed as shown in FIG. 4C while reduction of DX2 in p14/ARF-deficient cell lines (H322, H460, and A549) was observed as shown in FIG. 4D. In addition, p14/ARF-deficient cell lines were resistant to SLCB050 as shown in FIG. 5, whereas SCLC cell lines were sensitive to SLCB050. In particular, SLCB050 completely suppressed the H128 cell growth as shown in FIG. 6. In addition, HJH141204 and HJH141206 also suppressed cell viability as shown in FIG. 7, and accordingly, it was confirmed that rumor cell growth suppression was achieved by compound-DX2 binding.

It was evaluated whether SLCB050 was able to restore the sensitivity to the anticancer drug. As shown in FIG. 8A, resistance to GN 25 (synthesized as described in KR 1298168) in DX2 and DK MEF was abolished by co-treatment of SLCB050. In addition, as shown in FIG. 8B, resistance to Adriamycin in DX2 and DK MEF was abolished by co-treatment of Adriamycin (Adr) and SLCB050. In addition, as shown in FIG. 8C, SCLC cell line H69 was partially responded to SLCB050. However, as shown in FIG. 8C, p14/ARF deficient H322 did not show synergic response to combination treatment with SLCB050.

As shown in FIG. 9A, the tumor xenograft model using H446 was resistant to Adriamycin and partially responded to SLCB050. In addition, as shown in FIG. 9B, the increased tumor volume in the tumor xenograft model using H446 was moderately suppressed by SLCB050 injection (10 mg/kg, three times/week). In addition, the tumor inhibition effect was observed by injection of 5 mg/kg of Adriamycin (three times/week), but it evoked rapid weight loss and death. In contrast, combinational treatment with SLCB050 (10 mg/kg) showed more obvious anticancer effect as shown in FIG. 9B, despite low dosage (2.5 mg/kg) of Adriamycin treatment. Indeed, combinational treatment of Adriamycin and SLCB050 could obviously induce p53 expression in primary tumor cells obtained from DX2 or DK mouse as shown in FIG. 9C. These results indicate that inhibition of DX2 could enhance anticancer drug sensitivity through re-activation of p14/ARF.

To evaluate the anticancer effect of SLCB050 in a mouse model, SLCB050 was injected into DK mice according to an experimental schedule as shown in FIG. 10A. Combinational treatment of SLCB050 (10 mg/kg) and low dose (2.5 mg/kg) Adriamycin significantly suppressed tumor progression as shown in FIGS. 10B and 10C without significant weight loss. However, as shown in FIG. 10B, non-toxic dose of Adriamycin did not show anticancer effect on the mouse model.

More detailed histological analysis showed that SCLC region was more obviously erased by combinational treatment of Adriamycin and SLCB050 as shown in FIG. 11. As shown in FIG. 12A, under DX2-reduced condition upon SLCB050 treatment, apoptotic tumor cells were obviously increased as shown in FIGS. 12B and 12C. These results indicate that DX2 produced by aberrant splicing of AIMP2 promotes tumor progression, in particular, small cell lung cancer, via direct interaction and inhibition of p14/ARF as shown in FIG. 13. Thus, it was confirmed that small cell lung cancer would be treated by the compound inhibiting DX2-p14/ARF binding.

EXAMPLE 3

Comparative Measurement of AIMP2-DX2 Expression Levels in SCLC and NSCLC Cells

1. Cell Culture

NSCLC cell lines (A549,H1299, NCI-H23, NCI-H322, NCI-H358, and NCI-H460), HCT116 cell lines, and HEK293 cell lines were available from American Type Culture Collection (Manassas, Va.), and cultured in RPMI-1640 medium or DMEM supplemented with 10% FBS and 1% antibiotics.

NCI-H69, NCI-H128, and NCI-H146, which are SCLC cell lines, were purchased from Korean Cell Line Bank (Seoul, Korea), and cultured in a RPMI-1640 medium supplemented with 10% FBS.

2. Measurement of AIMP2-DX2 Expression Levels

Cells cultured in RIPA buffer (150 mM NaCl, 25 mM Tris-Cl, 1% NonidetP-40, 1% sodium deoxycholate, 0.1% sodium dodecyl sulfate, protease inhibitor cocktail) were suspended to separate proteins therefrom.

A sample including the separated proteins was thermally inactivated at a temperature of 95° C. for 7 minutes, and then, the resulting proteins were applied to SDS-PAGE, followed by western blot analysis according to a known method in the art (T. Mahmood, P. C. Yang. N. Am. J. Med. Science. 4: 429-434, 2012).

Commercially available Actin antibodies (sc-1616, Santa Cruz Biotechnology) were used, and AIMP2 and AIMP2-DX2 antibodies were prepared according to a conventional antibody preparation method.

Figure 14:
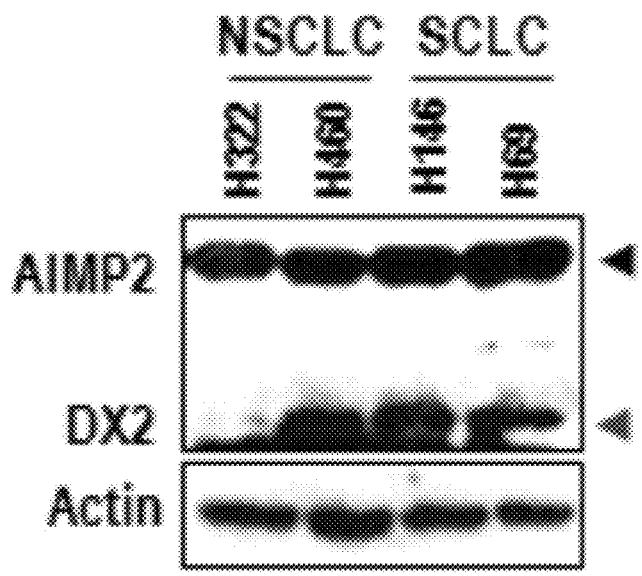
FIG. 14 shows results of measuring AIMP2-DX2 expression levels in various lung cancer cell lines (NSCLC: non small cell lung cancer cell line; SCLC: small cell lung cancer cell line; H322 and H460: NSCLC cell lines; H146 and H69: SCLC cell lines; AIMP2: aminoacyl tRNA synthetase complex-interacting multifunctional protein 2; and Actin: Actin)

As shown in FIG. 14, AIMP2-DX2 was similarly expressed in NSCLC cells and SCLC cells without a significant difference.

3. Measurement of AIMP2-DX2 Transcription

To measure ATMP2-DX2 transcription levels, NSCLC cells, such as A549, H1299, H23, H322, and H460, and SCLC cells, such as H146 and H69, were used. Primer sequences of SEQ ID NO: 1 or 2 listed in Table 1 were used to amplify ATMP2-DX2, and primer sequences of SEQ ID NO: 3 or 4 listed in Table 1 were used to amplify GAPDH.

Figure 15:
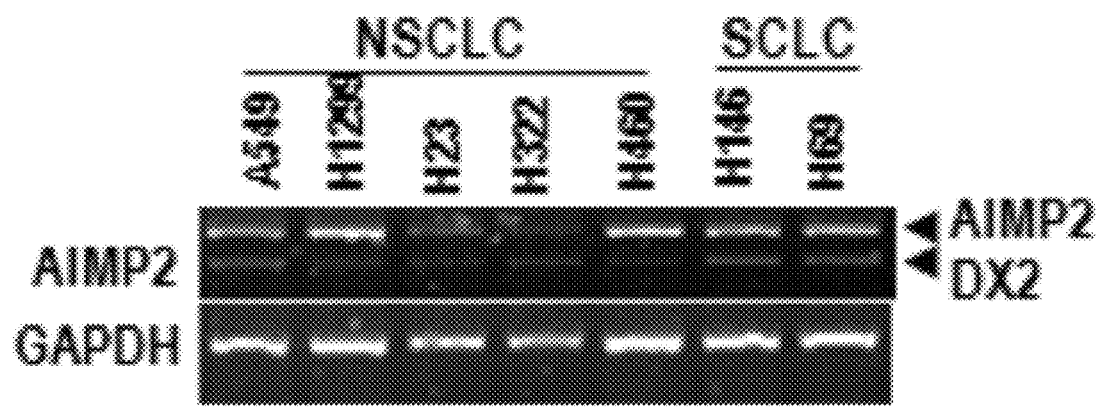
FIG. 15 shows results of measuring AIMP2-DX2 expression levels in various lung cancer cell lines (NSCLC: non small cell lung cancer cell line; SCLC: small cell lung cancer cell line; A549, H1299, H32, H322, and H460: NSCLC cell lines; H146 and H69: SCLC cell lines; AIMP2: aminoacyl tRNA synthetase complex-interacting multifunctional protein 2; GAPDH: Glyceraldehyde 3-phosphate dehydrogenase)

Consequently, as shown in FIG. 15, AIMP2-DX2 transcription levels were not different from those in SCLS cells and NSCLC cells.

TABLE 1

| Name of primer | Sequence | SEQ ID NO |
|---|---|---|
| Forward ATMP2-DX2 | 5'- AACGTGCACGGCAGGAGCTAC -3' | 1 |
| Reverse ATMP2-DX2 | 5'- CCAGCTGATAGTCTTGGCGGG -3' | 2 |

TABLE 1-continued

| Name of primer | Sequence | SEQ ID NO |
|---|---|---|
| Forward GAPDH | 5'- ATCTTCCAGGAGCGAGATCCC -3' | 3 |
| Reverse GAPDH | 5'- AGTGAGCTTCCCGTTCAGCTC -3' | 4 |

EXAMPLE 4

Figure 16:
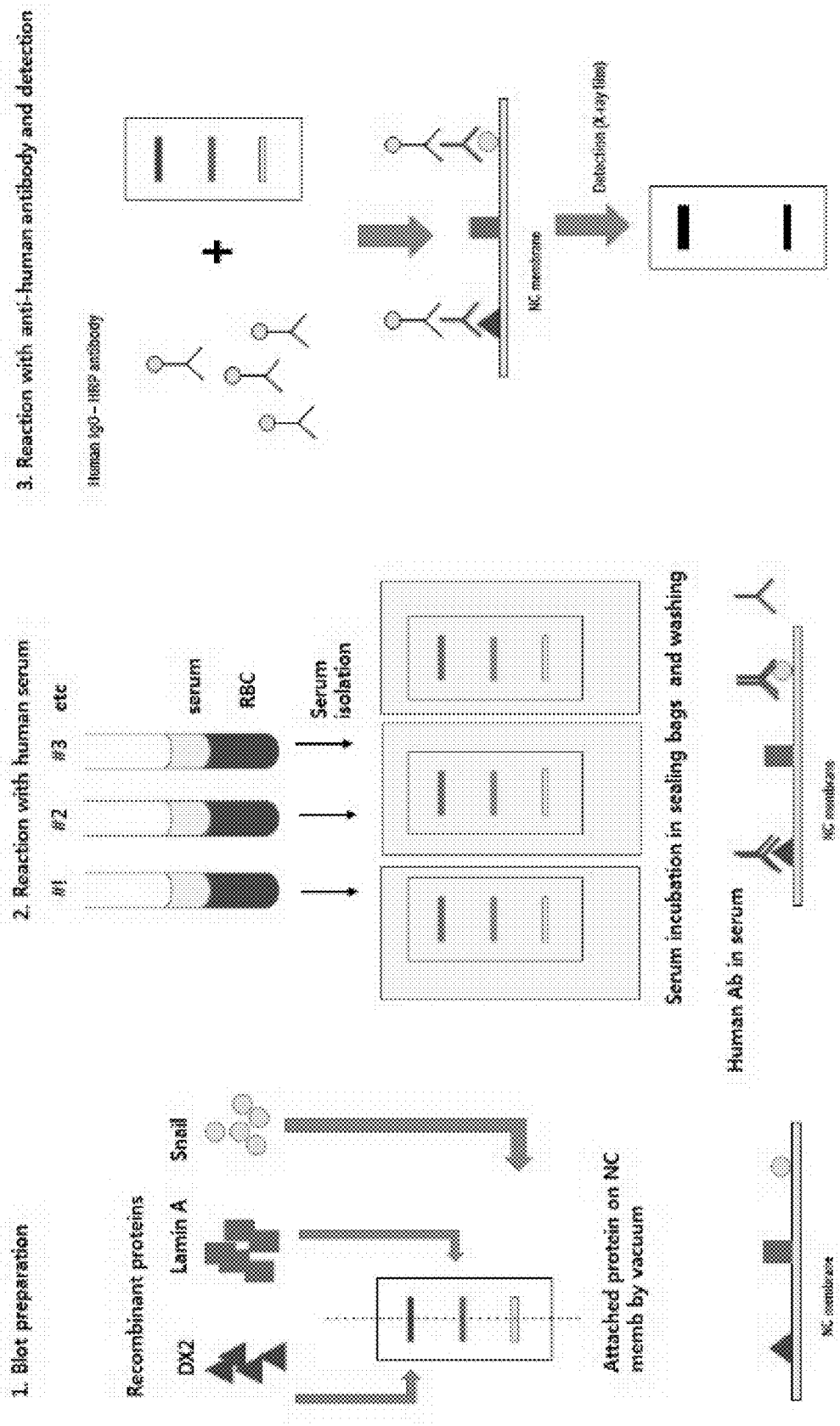
FIG. 16 is a schematic diagram of an experimental process for measuring ATMP2-DX2 autoantibody levels in serum of a patient with SCLC and NSCLS, wherein the experimental process consists of steps of preparing a diagnostic membrane (step 1), allowing a reaction with serum of a patient (stpep2), and allowing a reaction with anti-human antibody.

Measurement of AIMP2-DX2 Autoantibody Levels Serum of Patients With SCLC and NSCLS Sera of health individuals and patients with SCLC and NSCLC were available from Bucheon Hospital (schbc-biobank-2011-003). To measure anti-AIMP2-DX2 antibody levels, autoantibody levels were measured according to the experiment protocol shown in FIG. 16. Recombinant AIMP2-DX2, Lamin A, and Snail were each attached onto a nitrocellulose membrane (0.5 ng/well). Here, each membrane was incubated with a serum sample, which was diluted with blocking buffer at a ratio of 1:1000, for a reaction for 1 hour, and sequentially with (HRP)-conjugated anti-human antibodies (1:20,000) for 30 minutes. Then, sites on which human antibodies were attached were visualized by ECL in terms of chemiluminescence and X-ray film exposure.

Figure 17:
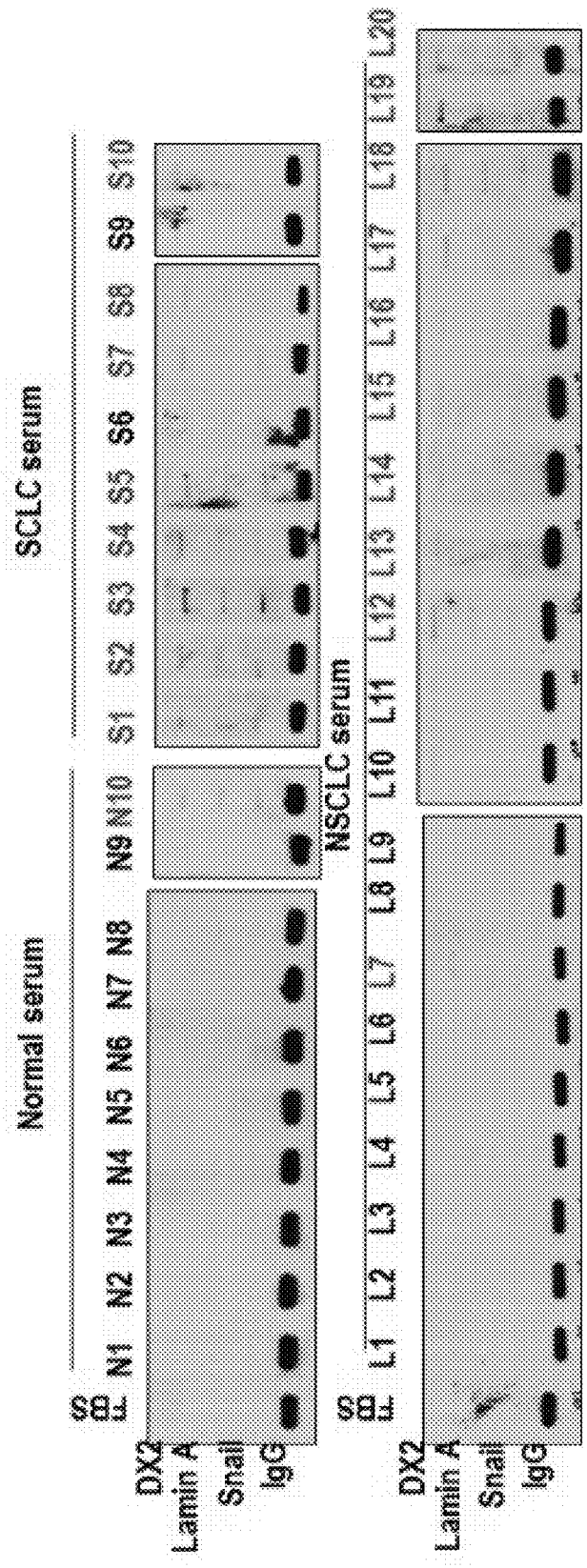
FIG. 17 shows results of measuring AIMP2-DX2 autoantibody levels in serum of a patient with SCLC and NSCLS (Normal serum, N1~N10: serum of a normal person; SCLC serum, S1~S10: serum of a patient with SCLC; NSCLC, L1~L20: serum of a patient with NSCLC; Lamin A: lamin A; and red color refers to a sample from which anti-AIMP2-DX2 antibodies were detected while black color refers to a sample from which anti-AIMP2-DX2 antibodies were not detected).

As a result, as shown in FIG. 17, AIMP2-DX2 autoantibodies were not detected at all in control group (healthy individuals) while they were detected in a group of patients with NSCLC or SCLC. In particular, in the case of a group of patients with SCLC (8 out of 10 cases) AIMP2-DX2 autoantibodies were detected, and thus, it was confirmed that AIMP2-DX2 autoantibodies were significantly highly detected in serum of a group of patients with SCLC.

However, SLCB050 of the present invention can be formulated in various forms according to purposes. In the following, embodiments of formulations using the compound of the present invention as an effective component are provided, but the present invention is not limited thereto.

FORMULATION EXAMPLE 1

Tablet (Direct Pressurization)

5.0 mg of SLCB050 was filtered through a sieve, and then, mixed with 14.1 mg of lactose, 0.8 mg of Crospovidone USNF, and 0.1 mg of magnesium stearate. A pressure was applied thereto to prepare the mixture in form of a tablet.

FORMULATION EXAMPLE 2

Tablet (Wet Granulation)

5.0 mg of SLCB050 was filtered through a sieve, and then, mixed with 16.0 mg of lactose and 4.0 mg of starch. A solution in which 0.3 mg of Polysorbate 80 was dissolved in pure water was added to the mixture in an appropriate amount, and then, the resulting solution was subjected to grain refining. After being dried, grains were filtered through a sieve, and then, mixed with 2.7 mg of colloidal silicon dioxide and 2.0 mg of magnesium stearate. A pressure was applied thereto to prepare the grains in form of a tablet.

FORMULATION EXAMPLE 3

Powder and Capsule 5.0 mg of SLCB050 was filtered through a sieve, and then, mixed with 14.8 mg of lactose, 10.0 mg of polyvinyl pyrrolidone, and 0.2 mg of magnesium stearate. The mixture was added to hard Gelatin Capsule Size 5 by using an appropriate device, thereby preparing the mixture in form of a capsule.

FORMULATION EXAMPLE 4

Injection 100 mg of SLCB050, 180 mg of mannitol, 26 mg of $Na_2HPO_4 12H_2O$, and 2.974 mg of distilled water were mixed together. A transparent glass ampoule was filled with the mixed solution, and then, sealed under an upper lattice by dissolving the glass. A sterilization process was performed thereon through autoclave at a temperature of 120° C. for at least 15 minutes, thereby preparing the mixture in form of injection.

It should be understood that embodiments described herein should be considered in a descriptive sense only and not for purposes of limitation. Descriptions of features or aspects within each embodiment should typically be considered as available for other similar features or aspects in other embodiments.

[Sequence List Free Text]

SEQ ID NO: 1 or 2 is a base sequence of a pair of primers for amplifying AIMP2-DX2.

SEQ ID NO: 3 or 4 is a base sequence of a pair of primers for amplifying GAPDH.

SEQ ID NO: 5 is an amino acid sequence of an AIMP2-DX2 protein.

SEQ ID NO: 6 is an amino acid sequence of an AIMP2-DX2 protein.

What is claimed is:

1. A method of treating a cancer disease in a subject, comprising:
   providing a pharmaceutical composition comprising, as an active ingredient, a compound represented by Formula 3:

[Formula 3]

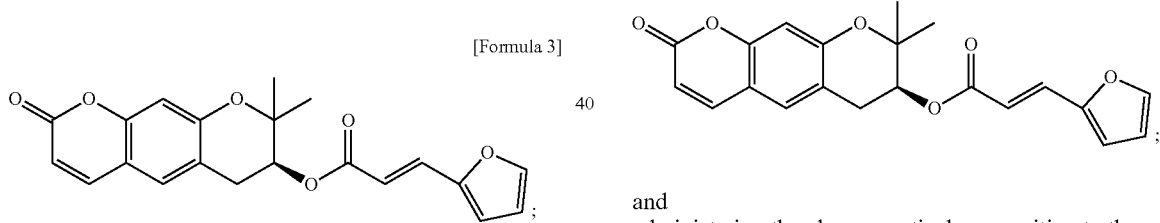

and
   administering the pharmaceutical composition to the subject, wherein the cancer disease is treated,
   wherein the cancer disease is selected from the group consisting of lung cancer, colorectal cancer, liver cancer, stomach cancer, esophageal cancer, pancreatic cancer, gallbladder cancer, kidney cancer, bladder cancer, prostate cancer, testis cancer, uterine cervical cancer, endometrial cancer, choriocarcinoma, ovarian cancer, breast cancer, thyroid cancer, brain cancer, head and neck cancer, malignant melanoma, lymphoma, and hematologic malignancy.

2. The method of claim 1, wherein the lung cancer is non-small cell lung cancer or small cell lung cancer.

3. A method of inhibiting drug resistance of an anticancer drug in a subject, comprising:

providing a pharmaceutical composition comprising, as an active ingredient, a compound represented by Formula 3:

[Formula 3]

and
   administering the pharmaceutical composition to the subject, wherein drug resistance of the anticancer drug is inhibited.

4. The method of claim 3, wherein the anticancer drug is selected from the group consisting of Adriamycin, Capecitabine, Caboplatin, Cisplatin, Oxaliplain, Cyclophosphamide, Docetaxel, Paclitaxel, Doxorubicin, Daunorubicin, Epirubicin, Idarubicin, Valrubicin, Mitoxantrone, Curcumin, Gefitinib, Erlotinib, Irinotecan, Topotecan, Vinblastine, Vincristine, Gemsitabin, Methotrexate, Trastzumab, Vinorelbine, Fluorouracil, and 3-(5, 8-dimethoxy-1,4-dioxonaphthalene-2-ylthio)propanoic acid.

5. The method of claim 3, wherein the compound inhibits binding between DX2 and p14/ARF proteins so that drug resistance of the anticancer agent is inhibited and anticancer effect of the anticancer agent is enhanced.

* * * * *